United States Patent
Maxwell et al.

(10) Patent No.: US 11,364,042 B2
(45) Date of Patent: *Jun. 21, 2022

(54) HISTOTRIPSY FOR THROMBOLYSIS

(71) Applicant: THE REGENTS OF THE UNIVERSITY OF MICHIGAN, Ann Arbor, MI (US)

(72) Inventors: Adam D. Maxwell, Ann Arbor, MI (US); Zhen Xu, Ann Arbor, MI (US); Hitinder S. Gurm, Ann Arbor, MI (US); Charles A. Cain, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 391 days.

This patent is subject to a terminal disclaimer.

(21) Appl. No.: 16/293,394

(22) Filed: Mar. 5, 2019

(65) Prior Publication Data
US 2019/0216478 A1 Jul. 18, 2019

Related U.S. Application Data

(63) Continuation of application No. 12/358,549, filed on Jan. 23, 2009, now Pat. No. 10,219,815, which is a (Continued)

(51) Int. Cl.
*A61B 17/22* (2006.01)
*A61B 17/225* (2006.01)
(Continued)

(52) U.S. Cl.
CPC .... *A61B 17/22004* (2013.01); *A61B 17/2258* (2013.01); *A61M 37/0092* (2013.01); (Continued)

(58) Field of Classification Search
CPC .......... A61B 17/22004; A61B 17/2258; A61B 2090/378; A61B 5/0536; A61B 5/055; (Continued)

(56) References Cited

U.S. PATENT DOCUMENTS 3,243,497 A  3/1966  Kendall et al.
3,679,021 A  7/1972  Goldberg et al.
(Continued)

FOREIGN PATENT DOCUMENTS

CN  1669672 A  9/2005
CN  1732031 A  2/2006
(Continued)

OTHER PUBLICATIONS

Sferruzza et al.; Generation of high power unipolar pulse with a piezocomposite transducer; In 1999 IEEE Ultrasonics Symposium Proceedings: International Symposium (Cat. No. 99CH37027); vol. 2; pp. 1125-1128; Oct. 17, 1999.
(Continued)

*Primary Examiner* — Hien N Nguyen
(74) *Attorney, Agent, or Firm* — Shay Glenn LLP

(57) ABSTRACT

Methods for performing non-invasive thrombolysis with ultrasound using, in some embodiments, one or more ultrasound transducers to focus or place a high intensity ultrasound beam onto a blood clot (thrombus) or other vascular inclusion or occlusion (e.g., clot in the dialysis graft, deep vein thrombosis, superficial vein thrombosis, arterial embolus, bypass graft thrombosis or embolization, pulmonary embolus) which would be ablated (eroded, mechanically fractionated, liquefied, or dissolved) by ultrasound energy. The process can employ one or more mechanisms, such as of cavitational, sonochemical, mechanical fractionation, or thermal processes depending on the acoustic parameters selected. This general process, including the (Continued)

Figure 1:
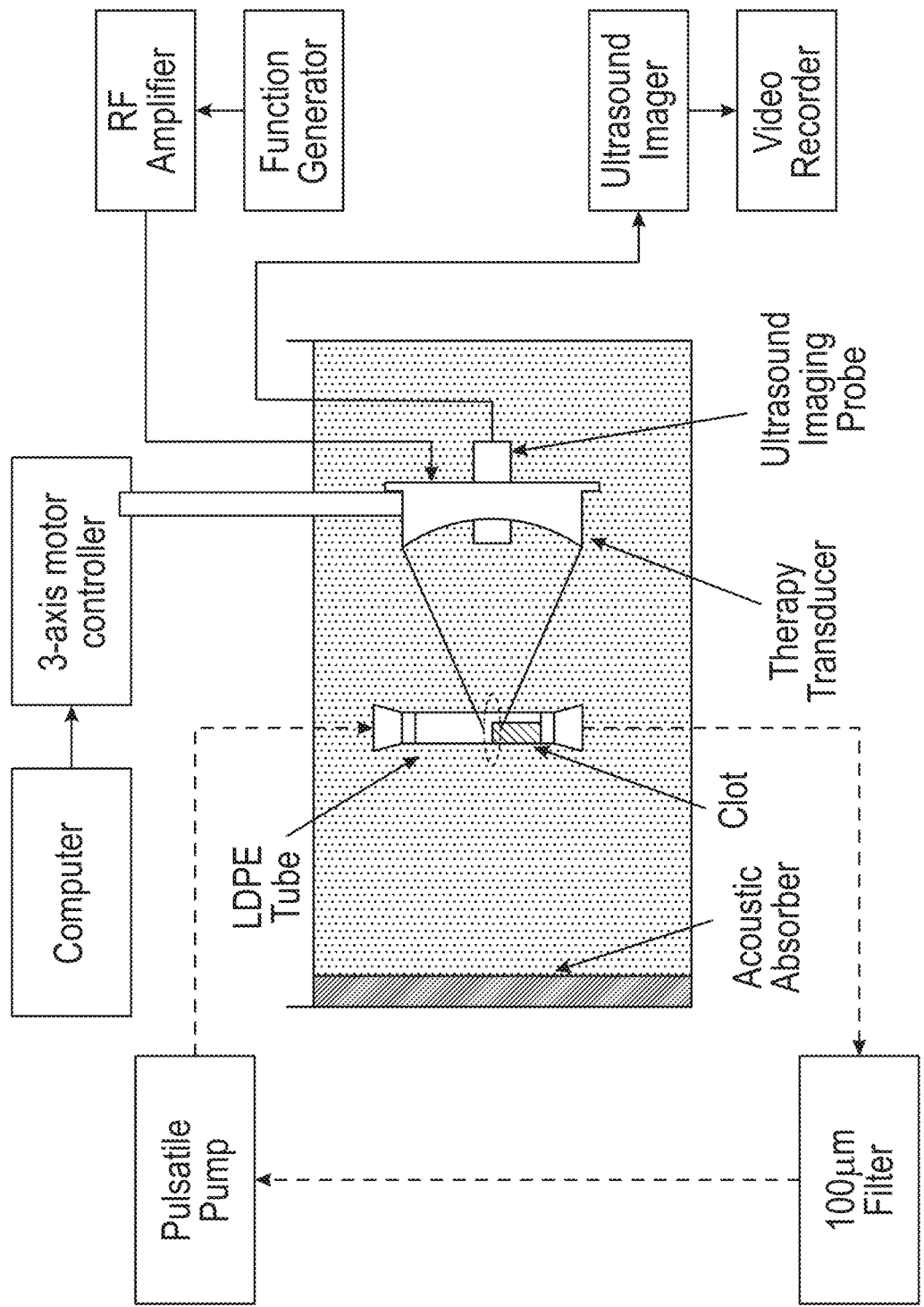

examples of application set forth herein, is henceforth referred to as "Thrombolysis."

6 Claims, 7 Drawing Sheets

Related U.S. Application Data continuation-in-part of application No. 12/121,001, filed on May 15, 2008, now Pat. No. 8,057,408, which is a continuation-in-part of application No. 11/523,201, filed on Sep. 19, 2006, now abandoned.

(60) Provisional application No. 60/786,322, filed on Mar. 27, 2006, provisional application No. 60/719,703, filed on Sep. 22, 2005, provisional application No. 60/753,376, filed on Dec. 22, 2005, provisional application No. 60/938,806, filed on May 18, 2007, provisional application No. 61/023,554, filed on Jan. 25, 2008.

(51) Int. Cl.
*A61M 37/00* (2006.01)
*A61B 5/0536* (2021.01)
*A61B 5/055* (2006.01)
*A61B 8/00* (2006.01)
*A61B 8/08* (2006.01)
*A61B 17/00* (2006.01)
*A61B 90/00* (2016.01)

(52) U.S. Cl.
CPC ............. *A61B 5/055* (2013.01); *A61B 5/0536* (2013.01); *A61B 8/00* (2013.01); *A61B 8/08* (2013.01); *A61B 8/485* (2013.01); *A61B 2017/00154* (2013.01); *A61B 2017/00172* (2013.01); *A61B 2017/00778* (2013.01); *A61B 2017/22001* (2013.01); *A61B 2017/22008* (2013.01); *A61B 2017/22088* (2013.01); *A61B 2017/22089* (2013.01); *A61B 2090/378* (2016.02)

(58) Field of Classification Search
CPC .. A61B 8/00; A61B 8/08; A61B 8/485; A61B 2017/00154; A61B 2017/00172; A61B 2017/00778; A61B 2017/22001; A61B 2017/22008; A61B 2017/22088; A61B 2017/22089; A61M 37/0092
See application file for complete search history.

(56) References Cited

U.S. PATENT DOCUMENTS

| | | |
|---|---|---|
| 3,879,699 A | 4/1975 | Pepper |
| 4,016,749 A | 4/1977 | Wachter |
| 4,024,501 A | 5/1977 | Herring et al. |
| 4,051,394 A | 9/1977 | Tieden |
| 4,117,446 A | 9/1978 | Alais |
| 4,266,747 A | 5/1981 | Souder, Jr. et al. |
| 4,269,174 A | 5/1981 | Adair |
| 4,277,367 A | 7/1981 | Madsen et al. |
| 4,351,038 A | 9/1982 | Alais |
| 4,406,153 A | 9/1983 | Ophir et al. |
| 4,440,025 A | 4/1984 | Hayakawa et al. |
| 4,447,031 A | 5/1984 | Souder, Jr. et al. |
| 4,453,408 A | 6/1984 | Clayman |
| 4,483,343 A | 11/1984 | Beyer et al. |
| 4,483,345 A | 11/1984 | Miwa |
| 4,548,374 A | 10/1985 | Thompson et al. |
| 4,549,533 A | 10/1985 | Cain et al. |
| 4,550,606 A | 11/1985 | Drost |
| 4,551,794 A | 11/1985 | Sandell |
| 4,575,330 A | 3/1986 | Hull |
| 4,622,972 A | 11/1986 | Giebeler, Jr. |
| 4,625,731 A | 12/1986 | Quedens et al. |
| 4,641,378 A | 2/1987 | McConnell et al. |
| 4,669,483 A | 6/1987 | Hepp et al. |
| 4,689,986 A | 9/1987 | Carson et al. |
| 4,757,820 A | 7/1988 | Itoh |
| 4,791,915 A | 12/1988 | Barsotti et al. |
| 4,819,621 A | 4/1989 | Ueberle et al. |
| 4,829,491 A | 5/1989 | Saugeon et al. |
| 4,856,107 A | 8/1989 | Dory |
| 4,865,042 A | 9/1989 | Umemura et al. |
| 4,888,746 A | 12/1989 | Wurster et al. |
| 4,890,267 A | 12/1989 | Rudolph |
| 4,922,917 A | 5/1990 | Dory |
| 4,938,217 A | 7/1990 | Lele |
| 4,957,099 A | 9/1990 | Hassler |
| 4,973,980 A | 11/1990 | Howkins et al. |
| 4,984,575 A | 1/1991 | Uchiyama et al. |
| 4,991,151 A | 2/1991 | Dory |
| 4,995,012 A | 2/1991 | Dory |
| RE33,590 E | 5/1991 | Dory |
| 5,014,686 A | 5/1991 | Schafer |
| 5,065,751 A | 11/1991 | Wolf |
| 5,080,101 A | 1/1992 | Dory |
| 5,080,102 A | 1/1992 | Dory |
| 5,091,893 A | 2/1992 | Smith et al. |
| 5,092,336 A | 3/1992 | Fink |
| 5,097,709 A | 3/1992 | Masuzawa et al. |
| 5,111,822 A | 5/1992 | Dory |
| 5,143,073 A | 9/1992 | Dory |
| 5,143,074 A | 9/1992 | Dory |
| 5,150,711 A | 9/1992 | Dory |
| 5,158,070 A | 10/1992 | Dory |
| 5,158,071 A | 10/1992 | Umemura et al. |
| 5,163,421 A | 11/1992 | Bernstein et al. |
| 5,165,412 A | 11/1992 | Okazaki |
| 5,174,294 A | 12/1992 | Saito et al. |
| 5,209,221 A | 5/1993 | Riedlinger |
| 5,215,680 A | 6/1993 | D'Arrigo |
| 5,219,401 A | 6/1993 | Cathignol et al. |
| 5,222,806 A | 6/1993 | Roberts |
| 5,230,340 A | 7/1993 | Rhyne |
| 5,295,484 A | 3/1994 | Marcus et al. |
| 5,316,000 A | 5/1994 | Chapelon et al. |
| 5,354,258 A | 10/1994 | Dory |
| 5,380,411 A | 1/1995 | Schlief |
| 5,393,296 A | 2/1995 | Rattner |
| 5,409,002 A | 4/1995 | Pell |
| 5,431,621 A | 7/1995 | Dory |
| 5,435,311 A | 7/1995 | Umemura et al. |
| 5,443,069 A | 8/1995 | Schaetzle |
| 5,450,305 A | 9/1995 | Boys et al. |
| 5,469,852 A | 11/1995 | Nakamura et al. |
| 5,474,071 A | 12/1995 | Chapelon et al. |
| 5,474,531 A | 12/1995 | Carter |
| 5,490,051 A | 2/1996 | Messana |
| 5,501,655 A | 3/1996 | Rolt et al. |
| 5,520,188 A | 5/1996 | Hennige et al. |
| 5,523,058 A | 6/1996 | Umemura et al. |
| 5,524,620 A | 6/1996 | Rosenschein |
| 5,540,909 A | 7/1996 | Schutt |
| 5,542,935 A | 8/1996 | Unger et al. |
| 5,558,092 A | 9/1996 | Unger et al. |
| 5,563,346 A | 10/1996 | Bartelt et al. |
| 5,566,675 A | 10/1996 | Li et al. |
| 5,573,497 A | 11/1996 | Chapelon |
| 5,580,575 A | 12/1996 | Unger et al. |
| 5,582,578 A | 12/1996 | Zhong et al. |
| 5,590,657 A | 1/1997 | Cain et al. |
| 5,601,526 A | 2/1997 | Chapelon et al. |
| 5,617,862 A | 4/1997 | Cole et al. |
| 5,648,098 A | 7/1997 | Porter |
| 5,666,954 A | 9/1997 | Chapelon et al. |
| 5,676,452 A | 10/1997 | Scholz |
| 5,676,692 A | 10/1997 | Sanghvi et al. |
| 5,678,554 A | 10/1997 | Hossack et al. |
| 5,694,936 A | 12/1997 | Fujimoto et al. |

(56) References Cited

U.S. PATENT DOCUMENTS

| | | |
|---|---|---|
| 5,695,460 A | 12/1997 | Siegel et al. |
| 5,717,657 A | 2/1998 | Ruffa |
| 5,724,972 A | 3/1998 | Petrofsky |
| 5,743,863 A | 4/1998 | Chapelon |
| 5,753,929 A | 5/1998 | Bliss |
| 5,759,162 A | 6/1998 | Oppelt et al. |
| 5,766,138 A | 6/1998 | Rattner |
| 5,769,790 A | 6/1998 | Watkins et al. |
| 5,797,848 A | 8/1998 | Marian et al. |
| 5,820,623 A | 10/1998 | Ng |
| 5,823,962 A | 10/1998 | Schaetzle et al. |
| 5,827,204 A | 10/1998 | Grandia et al. |
| 5,836,896 A | 11/1998 | Rosenschein |
| 5,849,727 A | 12/1998 | Porter et al. |
| 5,873,902 A | 2/1999 | Sanghvi et al. |
| 5,879,314 A | 3/1999 | Peterson et al. |
| 5,932,807 A | 8/1999 | Mallart |
| 5,947,904 A | 9/1999 | Hossack et al. |
| 6,001,069 A | 12/1999 | Tachibana et al. |
| 6,022,309 A | 2/2000 | Celliers et al. |
| 6,036,667 A | 3/2000 | Manna et al. |
| 6,088,613 A | 7/2000 | Unger |
| 6,093,883 A | 7/2000 | Sanghvi et al. |
| 6,113,558 A | 9/2000 | Rosenschein et al. |
| 6,126,607 A | 10/2000 | Whitmore, III et al. |
| 6,128,958 A | 10/2000 | Cain |
| 6,143,018 A | 11/2000 | Beuthan et al. |
| 6,165,144 A | 12/2000 | Talish et al. |
| 6,176,842 B1 | 1/2001 | Tachibana et al. |
| 6,296,619 B1 | 10/2001 | Brisken et al. |
| 6,308,585 B1 | 10/2001 | Nilsson et al. |
| 6,308,710 B1 | 10/2001 | Silva |
| 6,309,355 B1 | 10/2001 | Cain et al. |
| 6,318,146 B1 | 11/2001 | Madsen et al. |
| 6,321,109 B2 | 11/2001 | Ben-Haim et al. |
| 6,338,566 B1 | 1/2002 | Verdier |
| 6,344,489 B1 | 2/2002 | Spears |
| 6,391,020 B1 | 5/2002 | Kurtz et al. |
| 6,413,216 B1 | 7/2002 | Cain et al. |
| 6,419,648 B1 | 7/2002 | Vitek et al. |
| 6,470,204 B1 | 10/2002 | Uzgiris et al. |
| 6,488,639 B1 | 12/2002 | Ribault et al. |
| 6,490,469 B2 | 12/2002 | Candy |
| 6,500,141 B1 | 12/2002 | Irion et al. |
| 6,506,154 B1 | 1/2003 | Ezion et al. |
| 6,506,171 B1 | 1/2003 | Vitek et al. |
| 6,508,774 B1 | 1/2003 | Acker et al. |
| 6,511,428 B1 | 1/2003 | Azuma et al. |
| 6,511,444 B2 | 1/2003 | Hynynen et al. |
| 6,522,142 B1 | 2/2003 | Freundlich |
| 6,524,251 B2 | 2/2003 | Rabiner et al. |
| 6,536,553 B1 | 3/2003 | Scanlon |
| 6,543,272 B1 | 4/2003 | Vitek |
| 6,556,750 B2 | 4/2003 | Constantino et al. |
| 6,559,644 B2 | 5/2003 | Froundlich et al. |
| 6,576,220 B2 | 6/2003 | Unger |
| 6,599,288 B2 | 7/2003 | Maguire et al. |
| 6,607,498 B2 | 8/2003 | Eshel |
| 6,612,988 B2 | 9/2003 | Maor et al. |
| 6,613,004 B1 | 9/2003 | Vitek et al. |
| 6,613,005 B1 | 9/2003 | Friedman et al. |
| 6,626,854 B2 | 9/2003 | Friedman et al. |
| 6,626,855 B1 | 9/2003 | Weng et al. |
| 6,645,162 B2 | 11/2003 | Friedman et al. |
| 6,648,839 B2 | 11/2003 | Manna et al. |
| 6,666,833 B1 | 12/2003 | Friedman et al. |
| 6,685,640 B1 | 2/2004 | Fry et al. |
| 6,685,657 B2 | 2/2004 | Jones |
| 6,705,994 B2 | 3/2004 | Vortman et al. |
| 6,719,449 B1 | 4/2004 | Laugharn, Jr. et al. |
| 6,719,694 B2 | 4/2004 | Weng et al. |
| 6,735,461 B2 | 5/2004 | Vitek et al. |
| 6,736,814 B2 | 5/2004 | Manna et al. |
| 6,750,463 B1 | 6/2004 | Riley |
| 6,770,031 B2 | 8/2004 | Hynynen et al. |
| 6,775,438 B1 | 8/2004 | Gaedke et al. |
| 6,788,977 B2 | 9/2004 | Fenn et al. |
| 6,790,180 B2 | 9/2004 | Vitek |
| 6,820,160 B1 | 11/2004 | Allman |
| 6,852,082 B2 | 2/2005 | Strickberger et al. |
| 6,869,439 B2 | 3/2005 | White et al. |
| 6,890,332 B2 | 5/2005 | Truckai et al. |
| 6,929,609 B2 | 8/2005 | Asafusa |
| 7,004,282 B2 | 2/2006 | Manna et al. |
| 7,059,168 B2 | 6/2006 | Hibi et al. |
| 7,128,711 B2 | 10/2006 | Medan et al. |
| 7,128,719 B2 | 10/2006 | Rosenberg |
| 7,175,596 B2 | 2/2007 | Vitek et al. |
| 7,196,313 B2 | 3/2007 | Quinones |
| 7,223,239 B2 | 5/2007 | Schulze et al. |
| 7,258,674 B2 | 8/2007 | Cribbs et al. |
| 7,273,458 B2 | 9/2007 | Prausnitz et al. |
| 7,273,459 B2 | 9/2007 | Desilets et al. |
| 7,300,414 B1 | 11/2007 | Holland et al. |
| 7,311,679 B2 | 12/2007 | Desilets et al. |
| 7,331,951 B2 | 2/2008 | Eshel et al. |
| 7,341,569 B2 | 3/2008 | Soltani et al. |
| 7,347,855 B2 | 3/2008 | Eshel et al. |
| 7,358,226 B2 | 4/2008 | Dayton et al. |
| 7,359,640 B2 | 4/2008 | Onde et al. |
| 7,367,948 B2 | 5/2008 | O'Donnell et al. |
| 7,374,551 B2 | 5/2008 | Liang et al. |
| 7,377,900 B2 | 5/2008 | Vitek et al. |
| 7,429,249 B1 | 9/2008 | Winder et al. |
| 7,431,704 B2 | 10/2008 | Babaev |
| 7,442,168 B2 | 10/2008 | Novak et al. |
| 7,462,488 B2 | 12/2008 | Madsen et al. |
| 7,559,905 B2 | 7/2009 | Kagosaki et al. |
| 7,656,638 B2 | 2/2010 | Laakso et al. |
| 7,695,437 B2 | 4/2010 | Quistgaard et al. |
| 7,714,481 B2 | 5/2010 | Sakai |
| 7,771,359 B2 | 8/2010 | Adam |
| 7,967,763 B2 | 6/2011 | Deem et al. |
| 8,057,408 B2 | 11/2011 | Cain et al. |
| 8,337,407 B2 | 12/2012 | Quistgaard et al. |
| 8,342,467 B2 | 1/2013 | Stachowski et al. |
| 8,539,813 B2 | 9/2013 | Cain et al. |
| 8,568,339 B2 | 10/2013 | Rybyanets |
| 8,932,239 B2 | 1/2015 | Sokka et al. |
| 9,049,783 B2 | 6/2015 | Teofilovic |
| 9,061,131 B2 | 6/2015 | Jahnke et al. |
| 9,144,694 B2 | 9/2015 | Cain |
| 9,302,124 B2 | 4/2016 | Konofagou et al. |
| 9,526,923 B2 | 12/2016 | Jahnke et al. |
| 9,636,133 B2 | 5/2017 | Hall et al. |
| 9,642,634 B2 | 5/2017 | Cain et al. |
| 9,901,753 B2 | 2/2018 | Cain et al. |
| 9,943,708 B2 | 4/2018 | Roberts et al. |
| 10,046,181 B2 | 8/2018 | Barthe et al. |
| 10,071,266 B2 | 9/2018 | Cain |
| 10,130,828 B2 | 11/2018 | Vortman et al. |
| 10,219,815 B2 | 3/2019 | Maxwell et al. |
| 10,293,187 B2 | 5/2019 | Cannata et al. |
| 10,973,419 B2 | 4/2021 | Corl |
| 2001/0039420 A1 | 11/2001 | Burbank et al. |
| 2001/0041163 A1 | 11/2001 | Sugita |
| 2002/0045890 A1 | 4/2002 | Celliers et al. |
| 2002/0078964 A1 | 6/2002 | Kovac et al. |
| 2002/0099356 A1 | 7/2002 | Unger et al. |
| 2002/0145091 A1 | 10/2002 | Talish et al. |
| 2003/0092982 A1 | 5/2003 | Eppstein |
| 2003/0112922 A1 | 6/2003 | Burdette et al. |
| 2003/0149352 A1 | 8/2003 | Liang et al. |
| 2003/0157025 A1 | 8/2003 | Unger et al. |
| 2003/0169591 A1 | 9/2003 | Cochran |
| 2003/0181833 A1 | 9/2003 | Faragalla et al. |
| 2003/0199857 A1 | 10/2003 | Eizenhofer |
| 2003/0221561 A1 | 12/2003 | Milo |
| 2003/0236539 A1 | 12/2003 | Rabiner et al. |
| 2004/0122323 A1* | 6/2004 | Vortman .......... A61N 7/02 600/459 |
| 2004/0127815 A1 | 7/2004 | Marchitto et al. |
| 2004/0138563 A1 | 7/2004 | Moehring et al. |

(56) References Cited

U.S. PATENT DOCUMENTS

| | | |
|---|---|---|
| 2004/0162571 A1* | 8/2004 | Rabiner .......... A61N 7/022 606/159 |
| 2004/0236248 A1 | 11/2004 | Svedman |
| 2004/0243021 A1 | 12/2004 | Murphy et al. |
| 2004/0260214 A1 | 12/2004 | Echt et al. |
| 2005/0020945 A1 | 1/2005 | Tosaya et al. |
| 2005/0038339 A1 | 2/2005 | Chauhan et al. |
| 2005/0038361 A1 | 2/2005 | Zhong et al. |
| 2005/0152561 A1 | 7/2005 | Spencer |
| 2005/0154314 A1 | 7/2005 | Quistgaard |
| 2005/0154431 A1 | 7/2005 | Quistgaard et al. |
| 2005/0215901 A1 | 9/2005 | Anderson et al. |
| 2005/0234438 A1 | 10/2005 | Mast et al. |
| 2005/0283098 A1 | 12/2005 | Conston et al. |
| 2006/0060991 A1 | 3/2006 | Holsteyns et al. |
| 2006/0074303 A1 | 4/2006 | Chornenky et al. |
| 2006/0089636 A1 | 4/2006 | Christopherson et al. |
| 2006/0173387 A1 | 8/2006 | Hansmann et al. |
| 2006/0206028 A1 | 9/2006 | Lee et al. |
| 2006/0241466 A1 | 10/2006 | Ottoboni et al. |
| 2006/0241523 A1 | 10/2006 | Sinelnikov et al. |
| 2006/0241533 A1 | 10/2006 | Geller |
| 2006/0264760 A1 | 11/2006 | Liu et al. |
| 2006/0293630 A1 | 12/2006 | Manna et al. |
| 2007/0010805 A1 | 1/2007 | Fedewa et al. |
| 2007/0016039 A1 | 1/2007 | Vortman et al. |
| 2007/0044562 A1 | 3/2007 | Sarr |
| 2007/0065420 A1 | 3/2007 | Johnson |
| 2007/0083120 A1 | 4/2007 | Cain et al. |
| 2007/0161902 A1 | 7/2007 | Dan |
| 2007/0167764 A1 | 7/2007 | Hynynen |
| 2007/0205785 A1 | 9/2007 | Nilsson |
| 2007/0219448 A1 | 9/2007 | Seip et al. |
| 2008/0013593 A1 | 1/2008 | Kawabata |
| 2008/0033297 A1 | 2/2008 | Sliwa |
| 2008/0033417 A1 | 2/2008 | Nields et al. |
| 2008/0051656 A1 | 2/2008 | Vaezy et al. |
| 2008/0055003 A1 | 3/2008 | Unnikrishnan et al. |
| 2008/0082026 A1 | 4/2008 | Schmidt et al. |
| 2008/0091125 A1 | 4/2008 | Owen et al. |
| 2008/0126665 A1 | 5/2008 | Burr et al. |
| 2008/0177180 A1 | 7/2008 | Azhari et al. |
| 2008/0194965 A1 | 8/2008 | Sliwa et al. |
| 2008/0214964 A1 | 9/2008 | Chapelon et al. |
| 2008/0262345 A1 | 10/2008 | Fichtinger et al. |
| 2008/0262486 A1 | 10/2008 | Zvuloni et al. |
| 2008/0312561 A1 | 12/2008 | Chauhan |
| 2008/0319376 A1 | 12/2008 | Wilcox et al. |
| 2009/0030339 A1 | 1/2009 | Cheng et al. |
| 2009/0036773 A1 | 2/2009 | Lau et al. |
| 2009/0112098 A1 | 4/2009 | Vaezy et al. |
| 2009/0198094 A1 | 8/2009 | Fenster et al. |
| 2009/0211587 A1 | 8/2009 | Lawrentschuk |
| 2009/0227874 A1 | 9/2009 | Suri et al. |
| 2009/0230822 A1 | 9/2009 | Kushculey et al. |
| 2009/0287083 A1 | 11/2009 | Kushculey et al. |
| 2010/0011845 A1 | 1/2010 | Laugharn et al. |
| 2010/0056924 A1 | 3/2010 | Powers |
| 2010/0059264 A1 | 3/2010 | Hasegawa et al. |
| 2010/0069797 A1 | 3/2010 | Cain et al. |
| 2010/0125225 A1 | 5/2010 | Gelbart et al. |
| 2010/0152624 A1 | 6/2010 | Tanis et al. |
| 2010/0163694 A1 | 7/2010 | Fadler et al. |
| 2011/0118602 A1 | 5/2011 | Weng et al. |
| 2011/0319927 A1 | 12/2011 | Nita |
| 2012/0271223 A1 | 10/2012 | Khanna |
| 2013/0090579 A1 | 4/2013 | Cain et al. |
| 2013/0102932 A1 | 4/2013 | Cain et al. |
| 2013/0190623 A1 | 7/2013 | Bertolina et al. |
| 2013/0255426 A1 | 10/2013 | Kassow et al. |
| 2013/0303906 A1 | 11/2013 | Cain et al. |
| 2014/0073995 A1 | 3/2014 | Teofilovic et al. |
| 2014/0100459 A1 | 4/2014 | Xu et al. |
| 2014/0378832 A1 | 12/2014 | Sanghvi et al. |
| 2015/0224347 A1 | 8/2015 | Barthe et al. |
| 2015/0258352 A1 | 9/2015 | Lin et al. |
| 2015/0273246 A1 | 10/2015 | Darlington et al. |
| 2016/0135916 A1 | 5/2016 | Rakic et al. |
| 2016/0184616 A1 | 6/2016 | Cain et al. |
| 2017/0232277 A1 | 8/2017 | Hall et al. |
| 2018/0049719 A1 | 2/2018 | Xu et al. |
| 2018/0154186 A1 | 6/2018 | Xu et al. |
| 2019/0275353 A1 | 9/2019 | Cannata et al. |
| 2020/0346046 A1 | 11/2020 | Cannata et al. |

FOREIGN PATENT DOCUMENTS

| | | |
|---|---|---|
| CN | 201197744 Y | 2/2009 |
| CN | 102292123 A | 12/2011 |
| DE | 3220751 A1 | 12/1983 |
| DE | 3544628 A1 | 6/1987 |
| DE | 3817094 A1 | 11/1989 |
| DE | 4012760 A1 | 5/1992 |
| EP | 0017382 A1 | 10/1980 |
| EP | 0320303 A2 | 6/1989 |
| EP | 0332871 A2 | 9/1989 |
| EP | 0384831 A2 | 8/1990 |
| EP | 0755653 A1 | 1/1997 |
| EP | 1374785 A1 | 1/2004 |
| EP | 1504713 A1 | 2/2005 |
| GB | 2099582 A | 12/1982 |
| JP | 60-80779 A | 5/1985 |
| JP | 61-196718 A | 8/1986 |
| JP | 02-215451 A | 8/1990 |
| JP | H0422351 A | 1/1992 |
| JP | 06-197907 A | 7/1994 |
| JP | 07-504339 A | 5/1995 |
| JP | 08-84740 A | 4/1996 |
| JP | 06-304178 A | 5/1996 |
| JP | 08-131454 A | 5/1996 |
| JP | 09-55571 A | 2/1997 |
| JP | 10-512477 A | 12/1998 |
| JP | 2000300559 A | 10/2000 |
| JP | 2003510159 A | 3/2003 |
| JP | 2004505660 A | 2/2004 |
| JP | 2004249106 A | 9/2004 |
| JP | 2005167058 A | 6/2005 |
| JP | 2006511265 A | 4/2006 |
| JP | 2007144225 A | 6/2007 |
| JP | 2007520307 A | 7/2007 |
| JP | 2010019554 A | 1/2010 |
| JP | 2010029650 A | 2/2010 |
| JP | 2004512502 A | 4/2014 |
| WO | WO94/06355 A1 | 3/1994 |
| WO | WO02/32506 A1 | 4/2002 |
| WO | WO2005/018469 A1 | 3/2005 |
| WO | WO2008/051484 A2 | 5/2008 |

OTHER PUBLICATIONS

Akiyama et al.; Elliptically curved acoustic lens for emitting strongly focused finite-amplitude beams: Application of the spheroidal beam equation model to the theoretical prediction; Acoustical Science and Technology, vol. 26, pp. 279-284, May 2005.

Appel et al.; Stereoscopic highspeed recording of bubble filaments; Ultrasonics Sonochemistry; vol. 11(1); pp. 39-42; Jan. 2004.

Aschoff et al.; How does alteration of hepatic blood flow affect liver perfusion and radiofrequency-induced thermal lesion size in rabbit liver?; J Magn Reson Imaging; 13(1); pp. 57-63; Jan. 2001.

Atchley et al.; Thresholds for cavitation produced in water by pulsed ultrasound; Ultrasonics.; vol. 26(5); pp. 280-285; Sep. 1988.

Avtech; AVR-8 Data sheet; May 23, 2004; 3 pages; retrieved from the internet (http://www.avtechpulse.com).

Bjoerk et al.; Cool/MOS CP—How to make most beneficial use of the generation of super junction technology devices. Infineon Technologies AG. [retrieved Feb. 4, 2014] from the internet (http://www.infineon.com/dgdl/Infineon+-+Application+Note+-+PowerMOSFETs+-+600V+CoolMOS%E284%A2+-+CP+Most+beneficial+use+of+superjunction+technologie+devices.pdf?folderId=db3a304412b407950112b408e8c90004&fileId=db3a304412b407950112b40ac9a40688>pp. 1, 4, 14; Feb. 2007.

(56) References Cited

OTHER PUBLICATIONS

Bland et al.; Surgical Oncology; McGraw Hill; Chap. 5 (Cavitron Ultrasonic Aspirator); pp. 461-462; Jan. 29, 2001.
Burdin et al.; Implementation of the laser diffraction technique for cavitation bubble investigations; Particle & Particle Systems Characterization; vol. 19; pp. 73-83; May 2002.
Cain, Charles A.; Histotripsy: controlled mechanical sub-division of soft tissues by high intensity pulsed ultrasound (conference presentation); American Institute of Physics (AIP) Therapeutic Ultrasound: 5th International Symposium on Therapeutic Ultrasound; 44 pgs.; Oct. 27-29, 2005.
Chan et al.; An image-guided high intensity focused ultrasound device for uterine fibroids treatment; Medical Physics, vol. 29, pp. 2611-2620, Nov. 2002.
Clement et al.; A hemisphere array for non-invasive ultrasound brain therapy and surgery; Physics in Medicine and Biology, vol. 45, p. 3707-3719, Dec. 2000.
Cline et al.; Magnetic resonance-guided thermal surgery; Magnetic Resonance in Medicine; 30(1); pp. 98-106; Jul. 1993.
Curiel et al.; Elastography for the follow-up of high-intensity focused ultrasound prostate cancer treatment: Initial comparison with MRI; Ultrasound Med. Biol; 31(11); pp. 1461-1468; Nov. 2005.
Desilets et al.; The Design of Efficient Broad-Band Piezoelectric Transducers; Sonics and Ultrasonics, IEEE Transactions on, vol. 25, pp. 115-125, May 1978.
Emelianov et al.; Triplex ultrasound: Elasticity imaging to age deep venous thrombosis; Ultrasound Med Biol; 28(6); pp. 757-767; Jun. 2002.
Giannatsis et al.; Additive fabrication technologies applied to medicine and health care: a review; The International Journal of Advanced Manufacturing Technology; 40(1-2); pp. 116-127; Jan. 2009.
Gudra et al.; Influence of acoustic impedance of multilayer acoustic systems on the transfer function of ultrasonic airborne transducers; Ultrasonics, vol. 40, pp. 457-463, May 2002.
Hall et al.; A Low Cost Compact 512 Channel Therapeutic Ultrasound System for Transcutaneous Ultrasound Surgery; AIP Conference Proceedings, Boston, MA; vol. 829, pp. 445-449, Oct. 27-29, 2005.
Hall et al.; Imaging feedback of tissue liquefaction (histotripsy) in ultrasound surgery; IEEE Ultrasonic Symposium, Sep. 18-21, 2005, pp. 1732-1734.
Hartmann; Ultrasonic properties of poly(4-methyl pentene-1), Journal of Applied Physics, vol. 51, pp. 310-314, Jan. 1980.
Hobarth et al.; Color flow doppler sonography for extracorporal shock wave lithotripsy; Journal of Urology; 150(6); pp. 1768-1770; Dec. 1, 1993.
Holland et al.; Thresholds for transient cavitation produced by pulsed ultrasound in a controlled nuclei environment; J. Acoust. Soc. Am.; vol. 88(5); pp. 2059-2069; Nov. 1990.
Huber et al.; Influence of shock wave pressure amplitude and pulse repetition frequency on the lifespan, size and number of transient cavities in the field of an electromagnetic lithotripter; Physics in Medicine and Biology; vol. 43(10); pp. 3113-3128; Oct. 1998.
Hynynen et al.; Tissue thermometry during ultrasound exposure; European Urology; 23(Suppl 1); pp. 12-16; (year of pub. sufficiently earlier than effective US filing date and any foreign priority date)1993.
Kallel et al.; The feasibility of elastographic visualization of HIFU— induced thermal lesions in soft tissues: Image-guided high-intensity focused ultrasound; Ultrasound Med. Biol; 25(4); pp. 641-647; May 1999.
Kim et al.; Dependence of particle volume fraction on sound velocity and attenuation of EPDM composites; Ultrasonics, vol. 46, pp. 177-183, Feb. 2007.
Konofagou; Quo vadis elasticity imaging?; Ultrasonics; 42(1-9); pp. 331-336; Apr. 2004.
Krimholtz et al.; New equivalent circuits for elementary piezoelectric transducers; Electronics Letters, vol. 6, pp. 398-399, Jun. 1970.
Kruse et al.; Tissue characterization using magnetic resonance elastography: Preliminary results; Phys. Med. Biol; 45(6); pp. 1579-1590; Jun. 2000.
Lake et al.; Histotripsy: minimally invasive technology for prostatic tissue ablation in an in vivo canine model; Urology; 72(3); pp. 682-686; Sep. 2008.
Lauterborn et al.; Cavitation bubble dynamics studied by high speed photography and holography: part one; Ultrasonics; vol. 23; pp. 260-268; Nov. 1985.
Lensing et al.; Deep-vein thrombosis; The Lancet, vol. 353, pp. 479-485, Feb. 6, 1999.
Liu et al.; Viscoelastic property measurement in thin tissue constructs using ultrasound; IEEE Trans Ultrason Ferroelectr Freq Control; 55(2); pp. 368-383; Feb. 2008 (author manuscript, 37 pgs.).
Manes et al.; Design of a Simplified Delay System for Ultrasound Phased Array Imaging; Sonics and Ultrasonics, IEEE Transactions on, vol. 30, pp. 350-354, Nov. 1983.
Maréchal et al.; Effect of Radial Displacement of Lens on Response of Focused Ultrasonic Transducer; Japanese Journal of Applied Physics, vol. 46, p. 3077-3085; May 15, 2007.
Maréchal et al.; Lens-focused transducer modeling using an extended KLM model; Ultrasonics, vol. 46, pp. 155-167, May 2007.
Martin et al.; Water-cooled, high-intensity ultrasound surgical applicators with frequency tracking; Ultrasonics, Ferroelectrics and Frequency Control, IEEE Transactions on, vol. 50, pp. 1305-1317, Oct. 2003.
Miller et al.; A review of in vitro bioeffects of inertial ultrasonic cavitation from a mechanistic perspective; Ultrasound in Medicine and Biology; vol. 22; pp. 1131-1154; (year of publication is sufficiently earlier than the effective U.S. filing date and any foreign priority date) 1996.
Nightingale et al.; Analysis of contrast in images generated with transient acoustic radiation force; Ultrasound Med Biol; 32(1); pp. 61-72; Jan. 2006.
Ohl et al.; Bubble dynamics, shock waves and sonoluminescence; Phil. Trans. R. Soc. Lond. A; vol. 357; pp. 269-294; (year of publication is sufficiently earlier than the effective U.S. filing date and any foreign priority date) 1999.
Okada et al.; A case of hepatocellular carcinoma treated by MR-guided focused ultrasound ablation with respiratory gating; Magn Reson Med Sci; 5(3); pp. 167-171; Oct. 2006.
Parsons et al.; Cost-effective assembly of a basic fiber-optic hydrophone for measurement of high-amplitude therapeutic ultrasound fields; The Journal of the Acoustical Society of America, vol. 119, pp. 1432-1440, Mar. 2006.
Parsons et al.; Pulsed cavitational ultrasound therapy for controlled tissue homogenization; Ultrasound in Med. & Biol.; vol. 32(1); pp. 115-129; Jan. 2006.
Pishchalnikov et al.; Cavitation Bubble Cluster Activity in the Breakage of Kidney Stones by Lithotripter Shock Waves; J Endourol.; 17(7): 435-446; Sep. 2003.
Porter et al.; Reduction in left ventricular cavitary attenuation and improvement in posterior myocardial contrast . . . ; J Am Soc Echocardiography; pp. 437-441; Jul.-Aug. 1996.
Roberts et al.; Pulsed cavitational ultrasound: a noninvasive technology for controlled tissue ablation (histotripsy) in the rabbit kidney; Journal of Urology; vol. 175(2); pp. 734-738; Feb. 2006.
Rosenschein et al.; Ultrasound Imaging-Guided Noninvasive Ultrasound Thrombolysis: Preclinical Results; Circulation; vol. 102; pp. 238-245, Jul. 11, 2000.
Rowland et al.; MRI study of hepatic tumours following high intensity focused ultrasound surgery; British Journal of Radiology; 70; pp. 144-153; Feb. 1997.
Roy et al.; A precise technique for the measurement of acoustic cavitation thresholds and some preliminary results; Journal of the Acoustical Society of America; vol. 78(5); pp. 1799-1805; Nov. 1985.
Sapareto et al.; Thermal dose determination in cancer therapy; Int J Radiat Oncol Biol Phys; 10(6); pp. 787-800; Apr. 1984.
Sapozhnikov et al.; Ultrasound-Guided Localized Detection of Cavitation During Lithotripsy in Pig Kidney in Vivo; IEEE Ultrasonics Symposium, vol. 2; pp. 1347-1350; Oct. 7-10, 2001.

(56) References Cited

OTHER PUBLICATIONS

Sato et al.; Experimental Investigation of Phased Array Using Tapered Matching Layers. 2002 IEEE Ultrasound Symposium. vol. 2; pp. 1235-1238, Oct. 2002.

Simonin et al.; Characterization of heterogeneous structure in a polymer object manufactured by stereolithography with low-frequency microechography; Journal of Materials Chemistry; vol. 6, pp. 1595-1599, Sep. 1996.

Sokolov et al.; Use of a dual-pulse lithotripter to generate a localized and intensified cavitation field; Journal of the Acoustical Society of America; vol. 110(3); pp. 1685-1695; Sep. 2001.

Souchon et al.; Visualisation of HIFU lesions using elastography of the human prostate in vivo: Preliminary results; Ultrasound Med. Biol; 29(7); pp. 1007-1015; Jul. 2003.

Souquet et al.; Design of Low-Loss Wide-Band Ultrasonic Transducers for Noninvasive Medical Application; Sonics and Ultrasonics, IEEE Transactions on, vol. 26, pp. 75-80, Mar. 1979.

Toda; Narrowband impedance matching layer for high efficiency thickness mode ultrasonic transducers; Ultrasonics, Ferroelectrics and Frequency Control, IEEE Transactions on, vol. 49, pp. 299-306, Mar. 2002.

Van Kervel et al.; A calculation scheme for the optimum design of ultrasonic transducers; Ultrasonics, vol. 21, pp. 134-140, May 1983.

Wikipedia; Medical ultrasound; 15 pages; retrieved from the internet (https://en.wikipedia.org/w/index.php?title=Medical_utrasound&oldid=515340960) on Jan. 12, 2018.

Xie et al.; Correspondence of ultrasound elasticity imaging to direct mechanical measurement in aging DVT in rats; Ultrasound Med Biol; 31(10); pp. 1351-1359; Oct. 2005 (author manuscript, 20 pgs.).

Xu et al.; A new strategy to enhance cavitational tissue erosion by using a high intensity initiating sequence; IEEE Trans Ultrasonics Ferroelectrics and Freq Control; vol. 53(8); pp. 1412-1424; Aug. 2006.

Xu et al.; Controlled ultrasound tissue erosion: the role of dynamic interaction between insonation and microbubble activity; Journal of the Acoustical Society of America; vol. 117(1); pp. 424-435; Jan. 2005.

Xu et al.; Controlled ultrasound tissue erosion; IEEE Transaction on Ultrasonics, Ferroelectrics, and Frequency Control; vol. 51 (6); pp. 726-736; Jun. 2004.

Xu et al.; Effects of acoustic parameters on bubble cloud dynamics in ultrasound tissue erosion (histotripsy); Journal of the Acoustical Society of America; vol. 122(1); pp. 229-236; Jul. 2007.

Xu et al.; High Speed Imaging of Bubble Clouds Generated in Pulsed Ultrasound Cavitational Therapy Histotripsy; IEEE Trans Ultrason Ferroelectr Freq Control; ; vol. 54; No. 10; pp. 2091R2101; Oct. 2007.

Xu et al.; Investigation of intensity threshold for ultrasound tissue erosion; Ultrasound in Med. & Biol.; vol. 31(12); pp. 1673-1682; Dec. 2005.

Xu et al.; Optical and acoustic monitoring of bubble cloud dynamics at a tissue-fluid interface in ultrasound tissue erosion; Journal of the Acoustical Society of America; vol. 121(4); pp. 2421-2430; Apr. 2007.

Yan et al.; A review of rapid prototyping technologies and systems; Computer-Aided Design, vol. 28, pp. 307-318, Apr. 1996.

Cannata et al.; U.S. Appl. No. 16/698,587 entitled "Histotripsy systems and methods," filed Nov. 27, 2019.

XU et al.; U.S. Appl. No. 17/161,498 entitled Systems and methods for histotripsy immunosensitization, filed Jan. 28, 2021.

Cain et al.; U.S. Appl. No. 17/008,369 entitled "Histotripsy using very short ultrasound pulses," filed Aug. 31, 2020.

Bak; Rapid protytyping or rapid production? 3D printing processes move industry towards the latter; Assembly Automation; 23(4); pp. 340-345; Dec. 1, 2003.

Shung; Diagnostic Ultrasound: Imaging and Blood Flow Measurements; Taylor and Francis Group, LLC; Boca Raton, FL; 207 pages; (year of pub. sufficiently earlier than effective US filing date and any foreign priority date) 2006.

Xu et al.; U.S. Appl. No. 17/407,780 entitled "Histotripsy therapy systems and methods for the treatment of brain tissue," filed Aug. 20, 2021.

Macoskey; Acoustic methods for histotripsy feedback; (Dissertation): Biomedical Engineering and Science Computing; University of Michigan 2019; 207 pages; retrived from the internet (https://deepblue.lib.umich.edu/handle/2027.42/149988) on Feb. 2022.

\* cited by examiner

HISTOTRIPSY FOR THROMBOLYSIS

CROSS REFERENCE TO RELATED APPLICATIONS

This application is a continuation of U.S. patent application Ser. No. 12/358,549, filed Jan. 23, 2009, now U.S. Pat. No. 10,219,815, which is a continuation-in-part of U.S. patent application Ser. No. 12/121,001, filed May 15, 2008, now U.S. Pat. No. 8,057,408, which is a continuation-in-part of U.S. patent application Ser. No. 11/523,201 filed Sep. 19, 2006, now abandoned, which claims the benefit of U.S. Provisional Patent Application No. 60/786,322, filed Mar. 27, 2006, U.S. Provisional Patent Application No. 60/719,703, filed Sep. 22, 2005, and U.S. Provisional Patent Application No. 60/753,376, filed Dec. 22, 2005.

U.S. patent application Ser. No. 12/121,001 filed May 15, 2008, further claims the benefit of U.S. Provisional Patent Application No. 60/938,806, filed May 18, 2007.

U.S. patent application Ser. No. 12/358,549, filed Jan. 23, 2009, further claims the benefit of U.S. Provisional Application No. 61/023,554 filed Jan. 25, 2008. The entire disclosure of each of the above applications is incorporated herein by reference.

GOVERNMENT INTEREST

This invention was made with government support under Grant No. EB008998 awarded by the National Institutes of Health. The government has certain rights in the invention.

FIELD

The present teachings relate to ultrasound therapy and, more particularly, relate to methods and apparatus for performing "thrombolysis," as defined herein, in a safe, effective, noninvasive manner using direct image guidance.

BACKGROUND

This section provides background information related to the present disclosure which is not necessarily prior art.

Thrombosis is the medical term for the process of pathologic blood clot formation—the key mechanism underlying many cardiovascular diseases, including stroke, myocardial infarction, deep vein thrombosis (DVT), etc. These thrombi can break off from site of formation and travel to distant sites (embolisation) and cause symptoms at sites distinct from the site of formation. Further these processes may manifest in conduits that are placed in the vascular bed to bypass blood flow (e.g., grafts) or as extensions to the vascular bed (e.g., drive lines for cardiac assist devices, implantable venous catheters, etc.). Each of these conditions poses a significant clinical problem. For example, DVT is the formation of blood clots in the deep veins, most commonly those of the lower legs. DVT has an incidence rate of 1 in 1000 persons. Up to 5% of patients with DVT experience pulmonary embolism, which causes at least 100,000 deaths annually in the United States.

To treat thrombosis, the pathologic blood clot (thrombus) or clot fragment (embolus) needs to be removed. Current clinical treatments to remove thrombi include thrombolytic drugs, catheter-based surgical procedures, and direct surgical removal of clots. Treatment of thrombosis usually encompasses either breakup of the clot (thrombolysis) or removal (thrombectomy). These terms are used in reference to both thrombus and emboli irrespective of site of formation or disease and are used herein as such.

Thrombolytic drugs (e.g., rt-PA) dissolve the blood clot by breaking down the cross-linked fibrin structures that solidify the clot. Thrombolytic drugs systemically stimulate the fibrinolytic process while suppressing the anti-fibrinolytic process. Therefore, both thrombosis and normal hemostatic clot formation (vessel wound healing) are inhibited. Inhibition of normal hemostatic clot formation is associated with an increase in bleeding complications, which may be fatal in a small number of cases.

In contrast, treatments using catheter-based devices are localized to the target clot. The current catheter-based thrombolysis procedures include catheter-based local delivery of thrombolytic agents, vein segment isolation and thrombolysis, and mechanical disruption and aspiration of the clot (Rheolytic thrombectomy). However, catheter-based devices are invasive and carry an increased risk of bleeding, damage to the vessel wall, and infection. In rare cases, catheter-based thrombolysis methods may also result in death.

Direct surgical methods are even more invasive than catheter-based methods. Clinicians make a small incision through the skin and surgically remove the clot directly.

Researchers have been exploring new means to improve the efficiency and safety of thrombosis treatment techniques. Minimally invasive or non-invasive ultrasound methods to treat thrombosis have been developed.

Studies have shown that ultrasound energy can accelerate thrombolysis by facilitating the delivery of thrombolytic drugs to the target clot. Thrombolysis refers to dissolving or breaking up of a thrombus. For example, ultrasound combined with rt-PA can dissolve a clot within 30 minutes, which would otherwise take 3 hours using rt-PA alone. Ultrasound energy can be generated by inside the vessel through a catheter-based transducer (Rosenschein et al., U.S. Pat. No. 5,163,421, Tachibana et al., U.S. Pat. No. 6,001,069) or outside the patient body through an external transducer non-invasively (Holland et al., U.S. Pat. No. 7,300,414). Even though this method increases thrombolysis efficiency, it still carries the undesired side effects of thrombolytic drugs. This hybrid technique is still being studied and not currently in clinical use.

Recently, some researchers have been investigating the possibility of achieving thrombolysis using ultrasound alone or combined with contrast agents, without the use of pharmaceutical drugs. Using microbubbles induced by high intensity focused ultrasound (Rosenschein et al. U.S. Pat. Nos. 5,524,620 and 6,113,558) or via injected contrast agents (Unger et al., U.S. Pat. No. 6,576,220, Siegel et al., U.S. Pat. No. 5,695,460), blood clot removal can be achieved. Similarly, ultrasound energy can be generated inside the vessel or outside the patient body. However, the mechanism is not well understood, and therefore, these techniques remain far from clinical application.

Acoustic cavitation has been claimed to be a possible mechanism of some older ultrasound thrombolysis methods. Acoustic cavitation is a term used to define the interaction of an acoustic field, such as an ultrasound field, with bodies containing gas and/or vapor. This term is used in reference to the production of small cavities, or microbubbles, in the liquid. Specifically, when an acoustic field is propagated into a fluid, the stress induced by the negative pressure produced can cause the liquid to rupture, forming a void in the fluid which may contain vapor and/or gas. Acoustic cavitation also refers to the oscillation and/or collapse of microbubbles in response to the applied stress of the acoustic field.

However, no one has previously succeeded in achieving controlled and predictable cavitation for thrombolysis with real-time ultrasound feedback.

Methods have been developed to initiate, maintain, and control cavitation for use in general therapy. For example, Cain et al. (U.S. Pat. No. 6,309,355), which is hereby incorporated by reference, describes apparatus and methods that use cavitation induced by an ultrasound beam to create a controlled surgical lesion in a selected therapy volume of a patient.

As indicated, previous ultrasound thrombolysis methods involve the use of thrombolytic drugs or microbubbles. Other methods that use ultrasound energy alone, invasive methods or even noninvasive methods, do not allow easy assessment or feedback of when the process is operating effectively, and often do not provide any feedback which can be used to optimize the process. Consequently, more effective methods and techniques for ultrasound thrombolysis therapies are desirable and would enable beneficial noninvasive alternatives to many present methods in the thrombosis treatment field. In particular, monitoring treatment and receiving feedback during the procedure would inform a clinician whether the procedure is progressing adequately according to plan and when it can be ended. As such, the ability to monitor and adjust the ultrasound thrombolysis therapy concomitant with treatment would provide significant advantages over prior ultrasound thrombolysis therapies.

SUMMARY

This section provides a general summary of the disclosure, and is not a comprehensive disclosure of its full scope or all of its features.

According to the principles of the present teachings, novel ultrasound devices and methods for performing non-invasive thrombolysis with ultrasound are provided. Briefly, the method uses one or more ultrasound transducers to focus or place a high intensity ultrasound beam onto a blood clot or other vascular inclusion or occlusion (e.g., clot in the dialysis graft, deep vein thrombosis, superficial vein thrombosis, arterial embolus, bypass graft thrombosis or embolization, pulmonary embolus) which would be ablated (eroded, mechanically fractionated, liquefied, or dissolved) by ultrasound energy. The process can employ one or more mechanisms, such as of cavitational, sonochemical, mechanical fractionation, or thermal processes depending on the acoustic parameters selected. This general process, including the examples of application set forth herein, is henceforth referred to as "Thrombolysis."

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 illustrates an experimental apparatus for in-vitro thrombolysis. A blood clot is placed in an LDPE tube and the therapy transducer aligned with the focus at one end of the clot using a 3-axis positioning system. An ultrasound imager is located concentric with the therapy transducer for image-guidance during treatment. A 5 MHz single-element transducer to record backscatter was mounted perpendicular to the therapy transducer with their foci overlapping (not shown). The dashed lines show the connection of the circulatory flow system, when present. In static saline, the ends of the tube are plugged with rubber stoppers.

Figure 2:
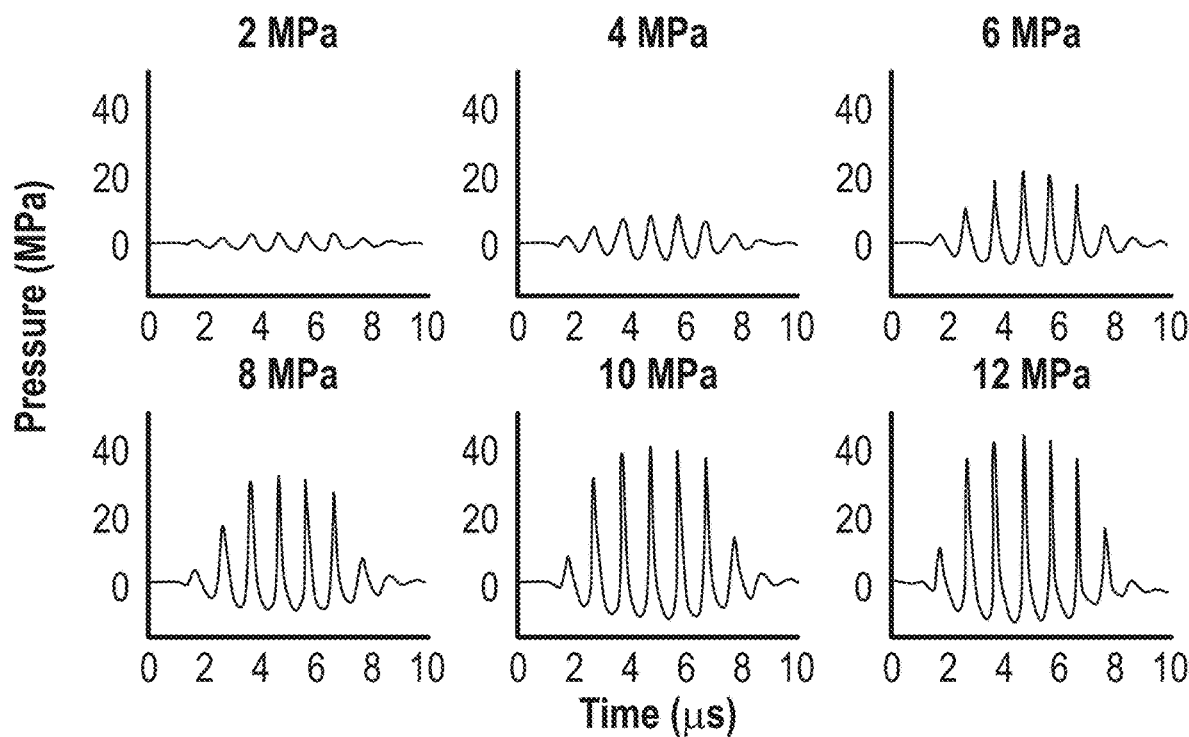

FIG. 2 illustrates pressure waveforms of therapy pulses at the focus of the transducer. The signals shown are averages of 200 pulses. The peak negative pressure is listed above each waveform. Measurements were recorded using a fiber optic probe hydrophone.

Figure 3:
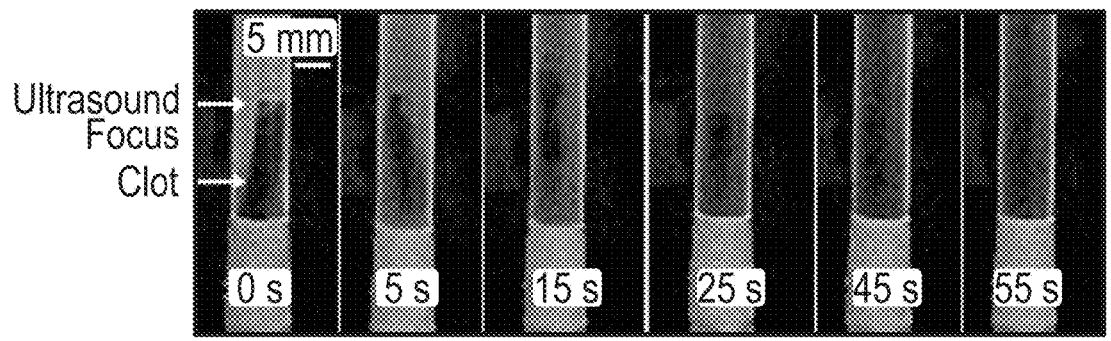

FIG. 3 illustrates progression of treatment in static saline. Ultrasound propagation is from right to left in the image. The clot moves into the focus of the transducer almost immediately after ultrasound exposure is started generated. The clot quickly loses mass and is bisected at the focus. Each of the two larger pieces is then dissolved over 45 seconds until no visible particles remain.

Figure 4A:
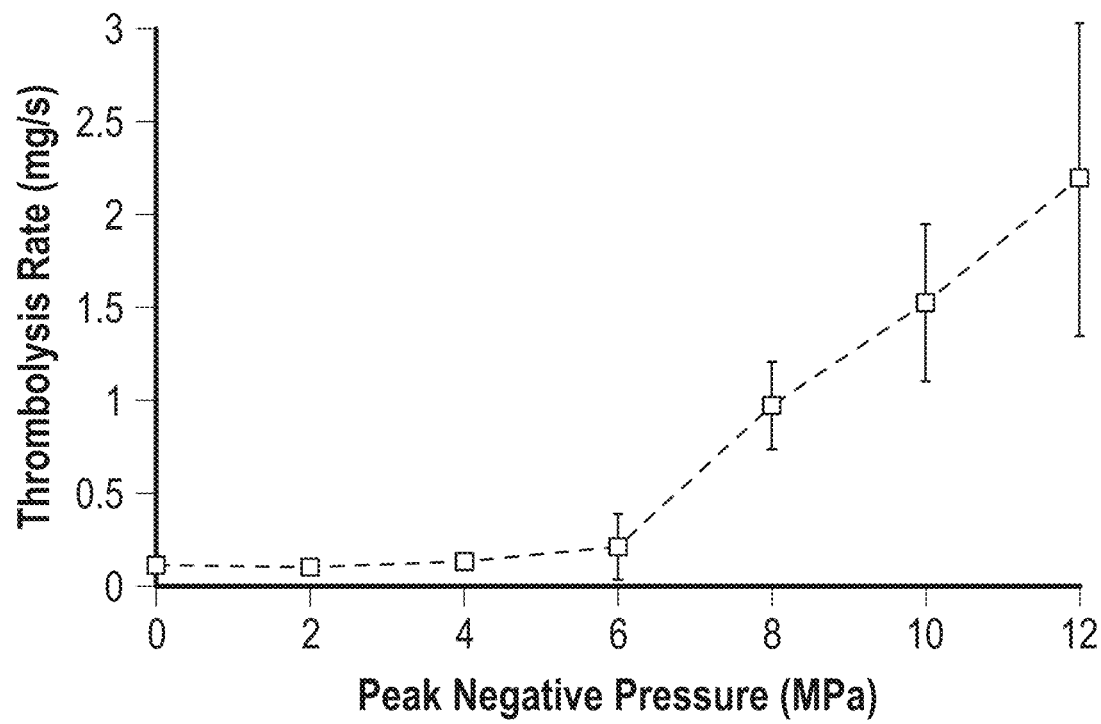
Figure 4B:
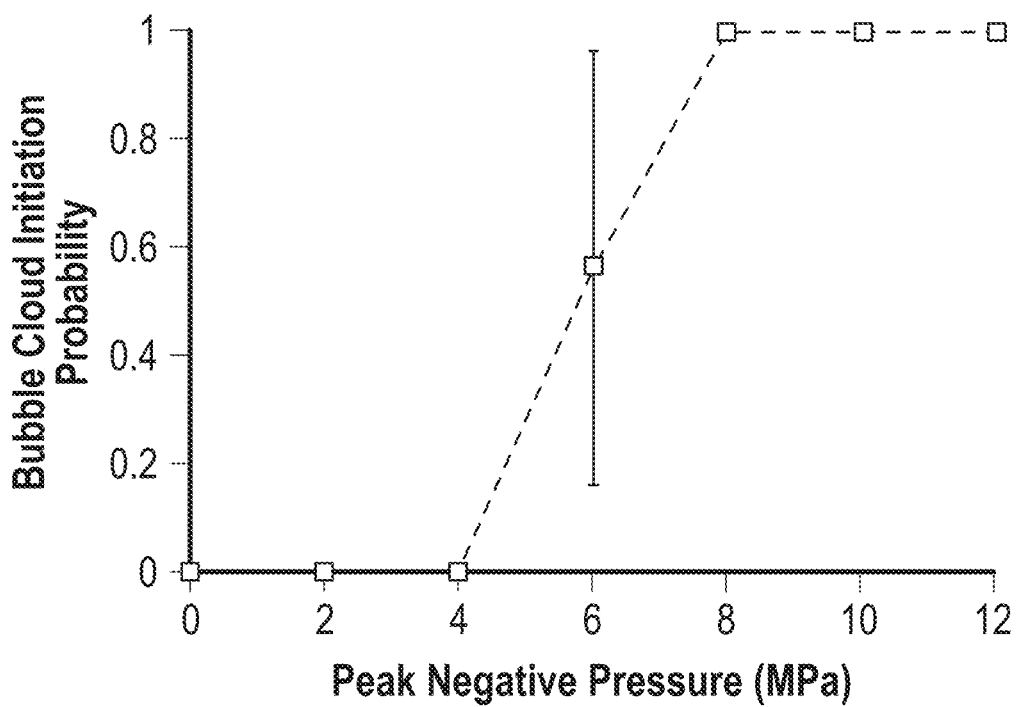

FIGS. 4(A) and 4(B) illustrate thrombolysis rate as a function of peak negative pressure at the therapy focus (mean+/−standard deviation, n=8). Pressures below 6 MPa had no observable effect on the clot after 5 minutes of treatment. At 6 MPa or greater, an increase in rate is observed, and the clot is quickly dissolved in times ranging between 80-300 seconds. (B) Percentage of initiated time versus peak negative pressure. The percentage of initiated time is defined as the initiated time divided by the total treatment time. Initiation here refers to the initiation of a temporally changing backscatter described in the text. For pressures <6 MPa, initiation was never detected. Above 6 MPa, initiation was always observed and the initiated state remained throughout the treatment.

Figure 5A:
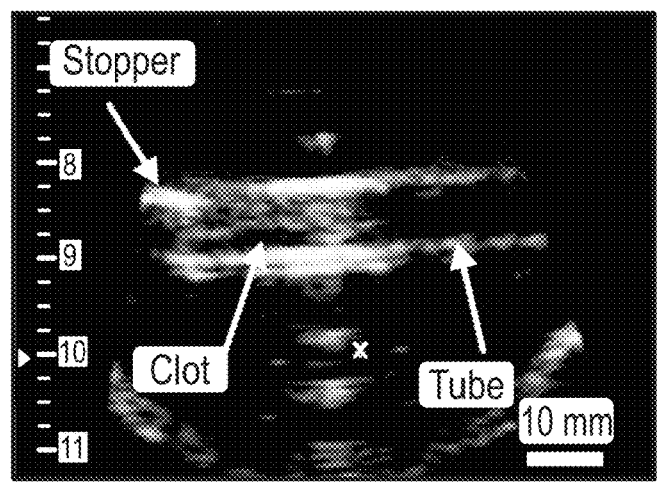
Figure 5B:
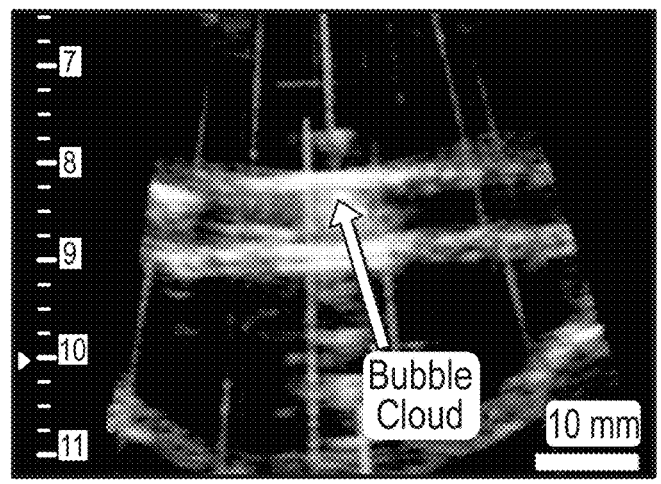
Figure 5C:
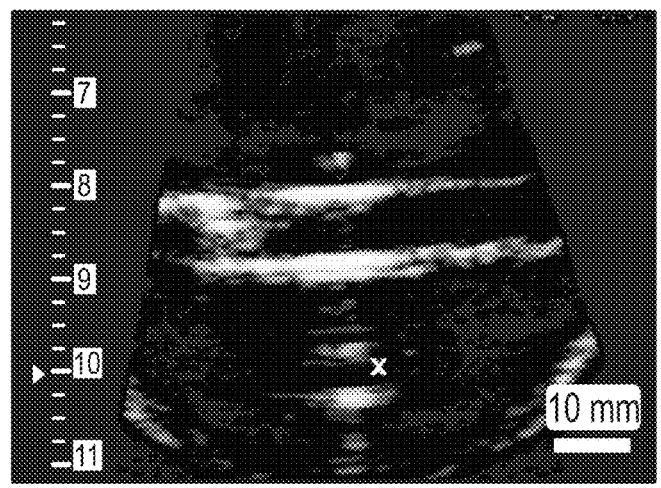

FIGS. 5(A)-5(C) illustrate B-Mode images of the histotripsy thrombolysis treatment using a 5 MHz imaging probe. The imaging probe is approximately 8 cm from the ultrasound focus. The ultrasound propagation is from top to bottom of the image. The clot is visible in the tube as an echogenic region prior to insonation (A). The bubble cloud is visible during treatment in (B). The vertical lines in (B) are acoustic interference of the therapy transducer with the imager. However, most of the image remains uncorrupted. The echogenicity of the clot is greatly reduced after complete thrombolysis (C).

Figure 6:
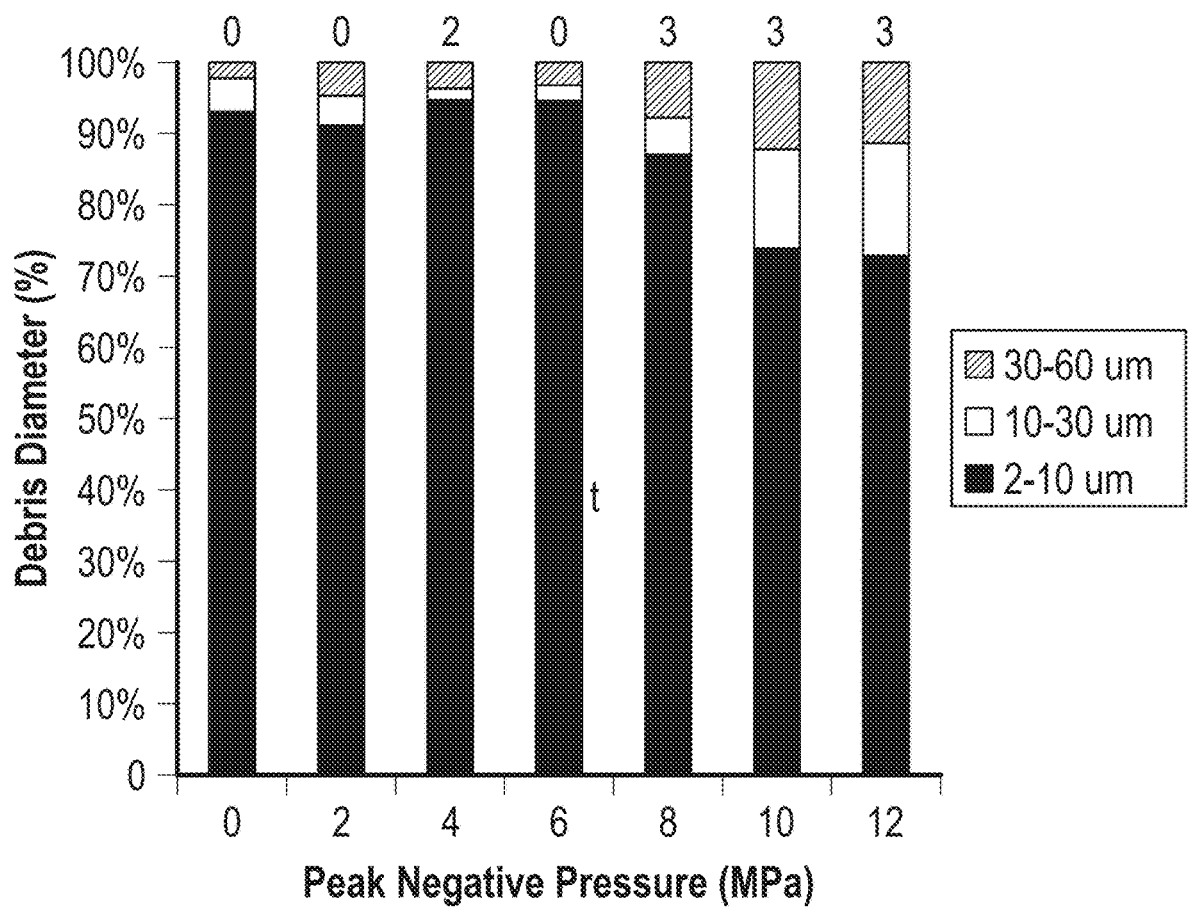

FIG. 6 illustrates debris volume distribution by particle diameter as measured by the Coulter Counter. A majority of the debris volume is smaller than 10 μm diameter for samples at all pressure levels. However, an increase in larger particles (30-60 μm) is apparent at 10 and 12 MPa. The number of measurements where the 100 μm tube was blocked (number of particles >60 um) is listed above each bar in the figure. There were 16 measurements taken at each pressure level.

Figure 7:
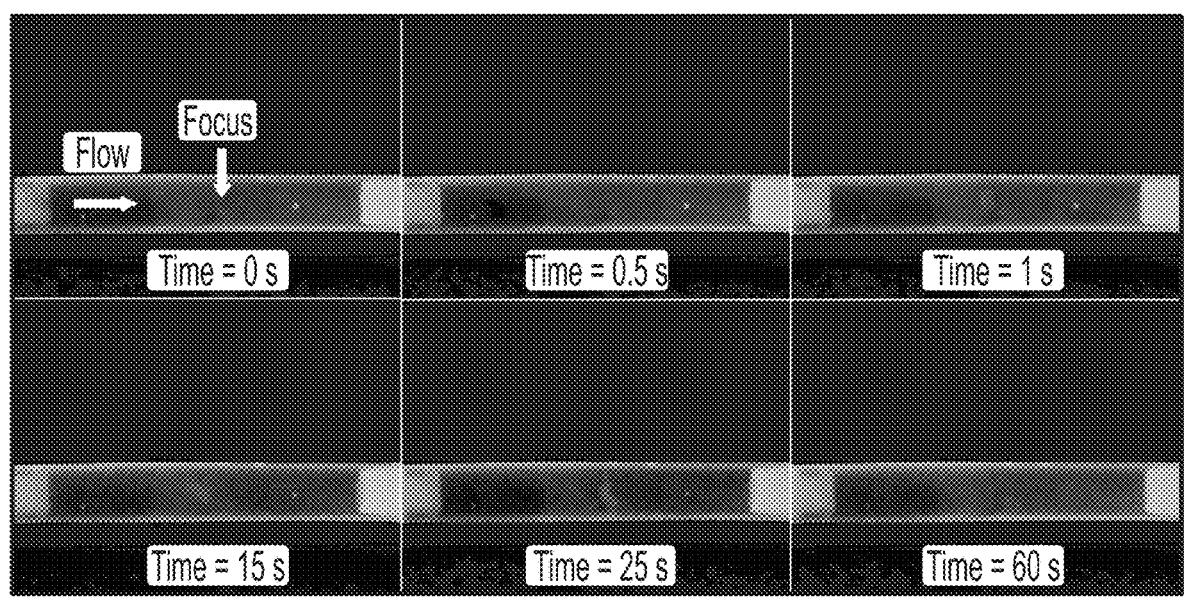
Figure 8A:
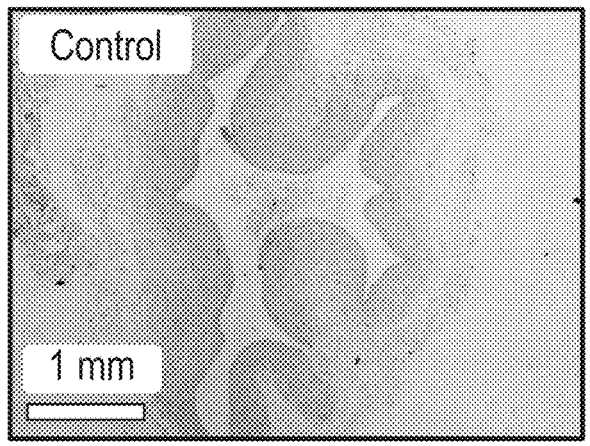
Figure 8B:
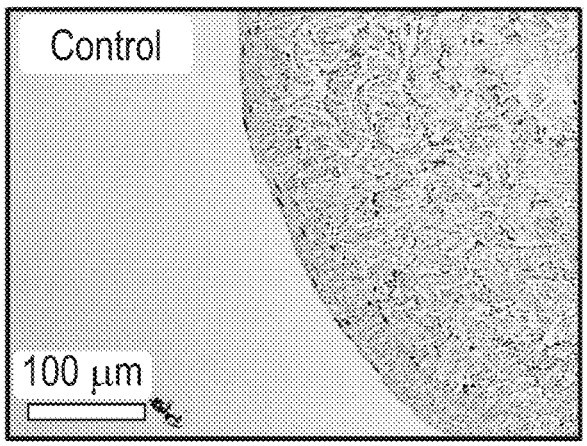
Figure 8C:
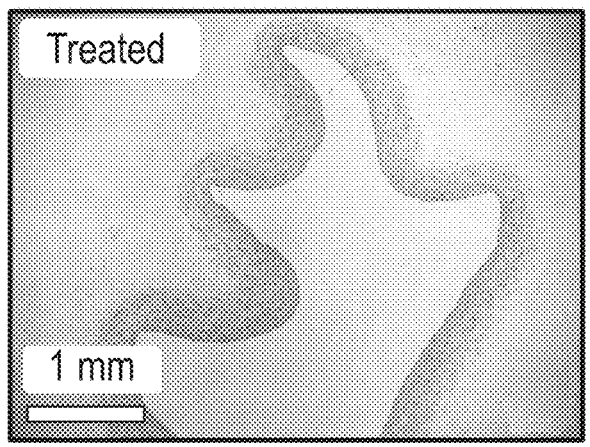
Figure 8D:
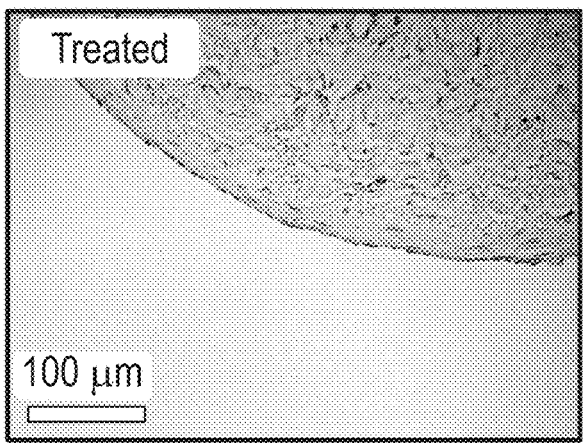

FIG. 7 illustrates progression of an experiment demonstrating the NET technique. Ultrasound propagation is from top to bottom. A clot fragment flows into the bubble cloud at the focus of the transducer generated prior to arrival of the fragment, with p− of 12 MPa. The clot fragment remains near the cloud at the transducer focus, and is further broken down over the course of 60 seconds. The bubble cloud is transparent and not visible in the images. The mean background flow rate is ~5 cm/s from left to right.

FIGS. 8(A)-(D) illustrate histological slides (H&E stain) from treatment of clots in canine inferior vena cava segments. A control sample is shown in (A) and a magnified view in (B). A treated sample exposed to 300 seconds of ultrasound at p− of 12 MPa is shown in (C) and a magnified view (D). Both samples were intact, and no discernable damage was observed to the treated vein wall.

Corresponding reference numerals indicate corresponding parts throughout the several views of the drawings.

DETAILED DESCRIPTION

Example embodiments will now be described more fully with reference to the accompanying drawings.

Thrombosis is the formation of a blood clot in vasculature and is the primary cause of many vascular diseases, including heart attack, stroke, pulmonary embolism (PE) and deep vein thrombosis (DVT). Current clinical methods to treat thrombosis include anticoagulant and thrombolytic drugs, catheter-based surgical techniques, or a combination of the two where a catheter is used to locally deliver the thrombolytic agent to the site of occlusion. Thrombolytic drugs (e.g., Streptokinase, urokinase, rt-PA etc.) administered without a catheter require long treatment times (several hours) and are non-specific, with a substantial risk of major bleeding that can be fatal in a small number of cases. The current catheter-based thrombolysis procedures include local delivery of thrombolytic agents by catheter, vein segment isolation and thrombolysis, and mechanical disruption and aspiration of the clot (rheolytic thrombectomy). Catheter-based devices have the advantage of localizing treatment to the clot, but are invasive and also carry an increased risk of hemorrhage, damage to the vessel wall, and infection. Surgical procedures also increase the cost of treatment due to additional patient care and monitoring post-operationally.

Ultrasound has been known for several decades to promote clot breakdown, as both a stand-alone procedure and used in conjunction with thrombolytic drugs or contrast agents. Many groups have reported an increase in thrombolytic efficiency of rt-PA and streptokinase when low-intensity, non-focused ultrasound was applied. A reduction in average lysis time from 3 hours to 30 minutes has been achieved for combined ultrasound+rt-PA therapy compared with just rt-PA alone. However, these methods still carry the risks of major bleeding associated with thrombolytic drugs. Alternatively, ultrasound has also been used by itself or in conjunction with catheters to locally administer thrombolysis. While catheter-based methods can quickly disrupt the occlusion, they also have the drawbacks associated with surgical techniques and may cause damage to the surrounding vessel. In-vitro studies have shown high-intensity focused ultrasound operated in a pulsed-mode induces rapid clot breakdown without thrombolytic drugs. Westermark et al. and Rosenschein et al. found that pulsing a focused transducer was more effective than either continuous-wave high-intensity ultrasound or lithotripsy shockwaves. The increased efficacy was attributed to activity of cavitation induced by the pulsing regime. The underlying mechanisms of cavitation damage, however, remain poorly understood.

In connection with the present disclosure, a new non-invasive thrombolysis method—histotripsy, which uses pulsed ultrasound alone—was investigated. This technology depends on control of cavitation to mechanically fractionate cells and tissues using focused ultrasound pulses. This technique can be viewed as soft tissue lithotripsy, giving rise to the name "histotripsy". The pulsed cavitational therapy process is similar to lithotripsy in that soft tissues are progressively mechanically subdivided instead of hard kidney stones. The present process of pulsed cavitational ultrasound is also referred to herein as histotripsy, connoting essentially the lithotripsy of soft tissues. The histotripsy process of the present teachings can, at least in part, involve the creation and maintenance of ensembles of microbubbles in the form of a bubble cloud and, in some embodiments, the use of feedback in order to optimize the process based on observed spatial-temporal bubble cloud dynamics.

It was found that cavitation nucleation can be controlled to create targeted tissue fractionation using appropriate ultrasound pulse sequences assisted by cavitation-based feedback monitoring. Histotripsy pulses include successive, very short (<50 cycles), high-pressure (>6 MPa) nonlinear pulses delivered at low duty cycles (0.1-5%). Cavitation can be monitored using acoustic feedback such as ultrasound backscatter.

It has been found that histotripsy can fractionate soft tissue to acellular debris within a few minutes. Histotripsy can be visualized and guided using real-time ultrasound imaging. The bubble cloud generated by histotripsy is visible as a highly-dynamic echogenic region on a B-Mode image, allowing precise targeting prior to treatment. The fractionated tissue shows a reduction in echogenicity compared with intact tissue, which can be used to evaluate progression of treatment. In vascular systems, Doppler ultrasound can also provide feedback and confirm restoration of flow after thrombolysis. The abilities to efficiently fractionate tissue and monitor therapy using image-guided real-time feedback are primary motivations to explore histotripsy as a potential non-invasive thrombolysis method.

Histotripsy thrombolysis method contains three general steps, all of which are guided by real-time imaging. First, the clot is targeted by the therapy focus prior to the treatment. Histotripsy pulses are used to create a bubble cloud without the presence of the clot, which appears on the image and is marked as the therapy focus. Targeting is achieved by moving the transducer to align the focus to the clot. Second, histotripsy treatment is applied using appropriate initiating and sustaining therapy ultrasound sequences. The treatment progress is monitored by detecting the bubble cloud, the clot and the blood flow in the vessel. Third, the treatment completion is determined by imaging the vessel and blood flow in the vessel.

A key part of the histotripsy process is that each incident ultrasound pulse has two primary functions. First, it produces a small fraction of the desired therapy result. Second, it predisposes the target volume to effective tissue interaction for the next pulse. A set of parameters, including but not limited to intensity, peak negative pressure, peak positive pressure, time of arrival, duration, and frequency, thus allows for many feedback, optimization, and real time monitoring opportunities.

Once initiated, each pulse produces a bubble cloud, or set of cavitationally active microbubbles, that, as indicated herein, produces part of the tissue therapy and produces microbubbles predisposing the volume to subsequent pulses. After initiation the process can progress with assurance that each pulse effectively participates in the therapy process. Each individual pulse breaks down a small portion of the thrombus and many pulses, from several thousand to over a million, are required to completely break down the whole clot.

Since each pulse produces a bubble cloud, it can be easily seen by ultrasound imaging scanners or by special transducers used to detect the ultrasound backscatter. In the case of the imaging systems, the bubbles show up as a bright spot on the image that can be localized to the desired place on the image by moving the therapy transducer focus either mechanically or via phased array electronic focus scanning. Because of the very short pulses (5 μs) and very low duty cycle (0.1%-5%), only a small number of ultrasound B-scan lines are corrupted by the histotripsy pulse interference. By comparison, most ultrasound therapy methods use long pulses (100 msec or longer) or continuous waves and ultrasound imaging during treatment is often completely corrupted by the interference of therapeutic ultrasound.

Pulsed cavitational ultrasound therapy, or the histotripsy process according to the present teachings, can include four sub-processes, namely: initiation, maintenance, therapy, and feedback, which are described in detail herein.

During the initiation step, cavitation nuclei are generated, placed, or seeded in the therapy volume, which is the portion of tissue to which the therapy is directed. The cavitation nuclei reduce the threshold for cavitation by subsequent therapy pulses. Without initiation, the therapy process will not proceed with typical therapy pulses. Initiation assures that the process will progress until it spontaneously (or through active intervention) extinguishes.

During the maintenance step, the presence of micro-nuclei in the therapy volume is actively maintained, assuring that subsequent therapy pulses will produce the appropriate tissue effect, breakdown of the thrombus in this disclosure. During the therapy step, the micro-nuclei (likely small microbubbles) that have been properly initiated and maintained by the preceding processes can be impinged upon by a therapy pulse that produces acute cavitation and tissue fractionation. Each therapy pulse can produce just a small part of the overall mechanical fractionation.

In the simplest process, the therapy transducer initiates, maintains, and produces the desired therapy effect. Thus, for example, a series of high intensity pulses are focused onto the therapy volume sufficient to initiate the bubble clouds. The intensity of the pulses can then be decreased to an intermediate intensity that is below a value that would not otherwise initiate the process. This intermediate intensity is sufficient to sustain the process, otherwise, the process can be re-initiated, if necessary, to produce adequate tissue fractionation. As will be described herein, feedback on the bubble cloud presence or absence can be obtained by monitoring the therapy pulse backscatter from the bubble cloud, where backscatter absence indicates an extinguished process. The backscatter is monitored by the therapy transducer (or subset of therapy transducer array elements) in the receive mode, or by a simple (and separate) monitoring transducer. In some embodiments, multiple transducers can be employed for monitoring feedback.

During the feedback step, each of the prior sub-processes can be monitored to thereby monitor overall therapy progression. The feedback and monitoring step allows for various parameters of the pulsed cavitational ultrasound process to be varied in real time or in stages, if desired, permitting controlled administration of the ultrasound therapy. For example, the process can be terminated, the extent of therapy measured, and the process reinitiated. In particular, the feedback sub-process enables adjustment and tuning of the histotripsy process in precise and controlled ways previously unobtainable.

It should be noted that methods of the present teachings can include variations where each of these four sub-processes can use different methods of energy delivery with different forms of energy and different feedback schemes. Additional details of various embodiments of each subprocess follow.

A. Initiation:

Initiation can comprise an initiation pulse sequence, which is also referred to herein as an initiation sequence or pulse, or initiation. Initiation introduces cavitation threshold-reducing cavitation nuclei and can be accomplished with a therapy transducer using acoustic energy, usually high intensity pulses, at the same frequency as the sustaining and therapy processes. However, initiation can be accomplished by other forms of energy including high intensity laser (or optical) pulses that create a vapor cloud or even a plasma cloud, or x-rays (the ionizing radiation bubble chamber effect). Cavitation nuclei can also be injected intravascularly, or can be injected, or shot (mechanically jetted) into the therapy volume. Thermal means can also be employed wherein elevated temperature, e.g., via a laser, can introduce vapor nuclei (boiling for example). Microbubbles (or proto-bubble droplets, e.g., perfluorocarbon droplets) can be targeted to a therapy volume by molecular or other recognition mechanisms, e.g., antibody against tumor antigens conjugated to nuclei (or proto-nuclei) that would concentrate in or near a tumor. Targeted substances can also be more general than microbubbles or proto-nuclei, such as enzymes, proteins, or other molecules or constructs that enhance the enucleation (gas bubble generation) of dissolved gas into actual microbubbles. Initiation can also occur via mechanical stimulation sufficient to generate cavitation or cavitation nuclei. Initiation, in some embodiments, can be accomplished by an ultrasound imaging transducer whose other role is obtaining feedback information on the histotripsy process or feedback on the therapy itself.

An effective acoustic approach is to use a separate acoustic transducer(s), which can be an array or a plurality of transducers, to initiate, and then use the therapy transducer for the maintenance and therapy sub-processes. This would enable one to use high frequency ultrasound for initiation thus making use of the higher resolution of high frequency transducers or arrays. In this embodiment, initiation could aid in determining the outlines of the therapy volume with high spatial resolution. Therapy could then progress at lower frequencies using the therapy transducer or an array of transducers. For example, lower frequencies would propagate through some bone and air. Thus, methods can include predisposing (initiating) with high resolution and disposing (providing therapy) at a lower frequency that can cover the entire therapy volume. Lower frequency sound propagates more easily through bone and air, enabling methods of the present teachings to be applied to sites beyond such structures. In addition, lower frequency sound has lower thermal absorption, reducing heat generation.

Feedback is important in determining if initiation has occurred because the therapy process will not progress without initiation. In some embodiments, feedback can include monitoring the backscattered signal from the therapy pulses. If no significant backscatter occurs, initiation has not been successful or the process has extinguished and needs to be re-initiated. In some embodiments, feedback can employ one or more of the following: an ultrasound imaging modality that would detect the microbubbles as a hyperechoic zone; a separate transducer to ping (send an interrogation pulse or pulses) and a transducer to receive it; optical processes wherein optical scattering from the microbubbles (when initiated) is detected; MRI imaging to detect the microbubbles; and low frequency hydrophones, which can detect the low frequency sound produced when bubble clouds expand and contract.

In some embodiments, the feedback scheme can determine the parameters of the existing cavitation nuclei and their dynamic changes with sufficient precision to predict the optimum characteristics or parameters for the next therapy pulse (intensity, peak negative pressure, peak positive pressure, time of arrival, duration, frequency, etc.).

B. Maintenance:

Maintenance can comprise a sustaining pulse sequence, which is also referred to herein as a sustaining sequence, sustaining or maintenance pulse, or maintenance. Maintenance can follow initiation and can also be part of initiation. Generally, once initiated, the cavitation process must be maintained or it will spontaneously extinguish. For example, cavitation can be extinguished when the next therapy pulse does not generate another bubble cloud or does not encounter sufficient nuclei to effectively cavitate at least a portion of the therapy volume. In various embodiments, maintenance is accomplished by the next therapy pulse that creates a bubble cloud that leaves behind sufficient nuclei for the following pulse.

Maintenance can also be accomplished by a separate sustaining transducer producing ultrasound to maintain (sustain) the appropriate nuclei characteristics and population. Thus, the separate transducer(s) described herein for initiation can also maintain (sustain) the nuclei. Likewise, in some embodiments, maintenance can be continued by optical means, x-rays (ionizing radiation), mechanical stimulation, or thermal means. In some embodiments, maintenance can be accomplished by a feedback ultrasound imaging transducer. For example, if a slow therapy pulse repetition frequency is desired (e.g., to prevent tissue heating), sustaining sequences or pulses (of lower intensity, for example) can be interleaved between the therapy pulses to sustain the microbubble or nuclei population and characteristics necessary to allow the next therapy pulse to be effective. These interleaved sustaining sequences can be applied by the various means enumerated herein for maintenance or initiation.

C. Therapy:

Therapy can comprise a therapy pulse sequence, which is also referred to herein as a therapy sequence, therapy pulse, or therapy. The therapy process is the interaction of ultrasound on existing cavitation nuclei to produce sufficiently vigorous cavitation to mechanically subdivide tissue within the therapy volume. Therapy energy in the histotripsy process can be acoustic (e.g., ultrasonic). The transducer or transducers can be either single focus, or multi-focus, or phased arrays where the focus can be scanned in 1, 2, or 3-dimensions. The therapy transducer(s) can be contiguous spatially or can be separated spatially, using multiple windows into the therapy volume. The transducers can also operate at different frequencies individually or as an overall ensemble of therapy transducers. The therapy transducer(s) can also be mechanically scanned to generate larger therapy zones and/or a combination of mechanically and electronically (phased array) scans can be used. The therapy transducer(s) can also be used, as outlined herein, as sources of initiation and/or maintenance processes and procedures. The therapy transducer(s) can be intimately involved in the feedback processes and procedures as sources of interrogation sequences or as receivers (or even imagers). Thus, in some embodiments, the therapy pulses (or sequences) can initiate, maintain, and do therapy.

The multiplicity of transducers enables various embodiments where one of the therapy transducers could operate at a significantly lower frequency from the other(s). For example, the higher frequency transducer can initiate (predispose) and the lower frequency transducer can do the mechanical fractionation (dispose).

D. Feedback & Monitoring:

In some embodiments, feedback enables assessment of parameters related to noninvasive image guided therapy or drug delivery. The methods and devices depend on the fact that the actual therapeutic effect is the progressive mechanical subdivision of the tissue that can also provide enhanced drug transport (or other therapeutic or diagnostic effect) over one or more therapy pulses. Thus, the tissues exposed to the histotripsy process are changed physically. These physical changes are much more profound than changes produced by competing therapies. Furthermore, embodiments of the present teachings make it possible to monitor the therapeutic effectiveness both during and after the therapy process, which been unobtainable in previous noninvasive therapy procedures.

In some embodiments, feedback and monitoring can include monitoring changes in: backscatter from bubble clouds; speckle reduction in backscatter; ultrasound Doppler; acoustic emissions, as described below.

Backscatter from Bubble Clouds: This feedback method can determine immediately if the histotripsy process has been initiated, is being properly maintained, or even if it has been extinguished. The method also can provide feedback permitting the histotripsy process to be initiated at a higher intensity and maintained at a much lower intensity. For example, backscatter feedback can be monitored by any transducer or ultrasonic imager. By measuring feedback for the therapy transducer, an accessory transducer can send out interrogation pulses. Moreover, the nature of the feedback received can be used to adjust acoustic parameters (and associated system parameters) to optimize the drug delivery and/or tissue erosion process.

Backscatter, Speckle Reduction: Progressively mechanically subdivided thrombus results in changes in the size and distribution of acoustic scatter. At some point in the process, the scattering particle size and density is reduced to levels where little ultrasound is scattered, or the amount scattered is reduced significantly. This results in a significant reduction in speckle, which is the coherent constructive and destructive interference patterns of light and dark spots seen on images when coherent sources of illumination are used; in this case, ultrasound. After some treatment time, the speckle reduction results in a dark area in the therapy volume. Since the amount of speckle reduction is related to the amount of tissue subdivision, it can be related to the size of the remaining tissue fragments. When this size is reduced to sub-cellular levels, no cells are assumed to have survived. So, treatment can proceed until a desired speckle reduction level has been reached. Speckle is easily seen and evaluated on standard ultrasound imaging systems. Specialized transducers and systems can also be used to evaluate the backscatter changes.

Ultrasound Doppler: Thrombi partially or completely occlude the blood vessel, reducing or completely stopping the blood flow in the vessel. By breaking down the thrombus, the blood flow would be gradually restored, which can be monitored using ultrasound Doppler. Doppler measures the flow in the vessel downstream of the treatment location. Complete restoration of the blood flow is the indication of treatment completion.

Acoustic Emission: As a tissue volume is subdivided, its effect on microbubbles is changed. For example, bubbles may grow larger and have a different lifetime and collapse changing characteristics in intact versus fluidized tissue. Bubbles may also move and interact after tissue is subdivided producing larger bubbles or cooperative interaction among bubbles, all of which can result in changes in acoustic emission. These emissions can be heard during treatment and they change during treatment. Analysis of these changes, and their correlation to therapeutic efficacy, enables monitoring of the progress of therapy.

E. Acoustic Manipulation

In addition to breaking down thrombus, histotripsy has the ability to manipulate (e.g., trapping, moving, or rotating) an object in or near the focal location or target area in the presence or absence of a background flow (e.g., blood flow). In some embodiments, this manipulation is achieved using acoustic energy only, and therefore, is termed acoustic manipulation. It should be appreciated that in some embodiments acoustic manipulation can use other forces, such as background flow, or structure, such as vessel walls, to aid in the manipulation of the object.

To achieve acoustic trapping, a bubble cloud is generated in a tube-like structure (e.g., blood vessel) in the presence of a directional flow. As one or more bubbles expand and contract or collapses, alternating inward and outward fluid flow producing microstreaming. Activated by our short, intense histotripsy pulses, the collective expansion, contraction, and collapse of the bubble cloud occur extremely fast (on the order of microseconds), which result in significant fluid flow. It interacts with tube walls and causes a vortex-like flow that directs to the center of the bubble cloud. This fluid flow is maintained by histotripsy pulses and stops immediately when the histotripsy pulses end. When an object flows into the bubble cloud in the presence of the background flow, if the fluid flow rate is higher than the background flow, the object can be captured and trapped by the bubble cloud.

If the ultrasound pressure used to generate the bubble cloud is above the cavitation threshold to cavitate and damage the object, histotripsy can simultaneously fractionate and trap the object (e.g., blood clot).

To achieve acoustic moving, the bubble cloud location is moved by changing the position of the acoustic beam, which is realized by mechanically moving the therapy ultrasound transducer or electronically moving the transducer focus. Since the object is trapped in the bubble cloud, the object is moved with the cloud.

Rotational fluid flow may be created by a bubble cloud and its interaction with surrounding physical boundaries (e.g., liquid/solid boundaries). This flow results in rotation of the object in the bubble cloud, which is termed acoustic rotation.

Acoustic manipulation has clinical significance when applied to the thrombolysis application. For example, there is a concern that large clot fragments escape from the histotripsy thrombolysis treatment region and occlude the vessels causing hazardous embolization. Using acoustic trapping, a Non-invasive Embolus Trap (NET) is developed to prevent embolization caused by escaping clot fragments. The NET uses a secondary cavitating bubble cloud (or more bubble clouds) placed downstream of the treatment location, to capture and fractionate any clot fragments escaping the primary treatment cloud.

Acoustic manipulation also has a wider application outside thrombolysis. Acoustic manipulation can be used on an object other than a thrombus or thrombus fragment, e.g., bead, nano-particle, non-thrombotic emboli, arterial plaque, air bubbles, etc. For example, we can acoustically trap a bead encapsulating therapeutic agents such as pharmaceutics in a blood stream, acoustically move the bead to a treatment location (e.g., a tumor), delivery histotripsy treatment to fractionate the bead and release the therapeutic agents.

In connection with the present disclosure, the preliminary feasibility of the histotripsy thrombolysis technique was evaluated in a vessel model with static saline. The rate of thrombolysis versus pressure level was measured to assess efficiency. Cavitating bubble clouds were monitored using acoustic backscatter and correlated to the thrombolysis rate. Since circulatory flow in-vivo may have an effect on cavitation activity, the treatment was performed in a fast, pulsatile flow model. As histotripsy mechanically breaks down clots to debris particles, there is a concern that the debris may break off causing hazardous emboli that can occlude blood vessels and cause significant tissue ischemia with resultant morbidity and rarely mortality. To evaluate the risk of embolism, the sizes of clot debris generated by the procedure was measured. In addition, the use of a secondary cavitating bubble cloud as a non-invasive emboli filter was tested by capturing and further fractionating larger clot fragment.

Methods

A. Clot Formation

Fresh whole canine blood was obtained from research subjects and a citrate-phosphate-dextrose (CPD) solution (#C1765, Sigma-Aldrich Co., St. Louis, Mo.) was immediately added as an anti-coagulant at a ratio of 1 mL CPD per 9 mL blood. The blood was stored at 4° C. for up to three days prior to use. To induce clotting, a 0.5 M $CaCl_2$ standard solution (#21107, Sigma-Aldrich Co., St. Louis, Mo.) was mixed with the blood, using 0.05 mL $CaCl_2$ per 1 mL blood. The blood was drawn in 0.4 mL volumes into 1 mL syringes to form cylindrical clots with approximate dimensions of 4 mm (diameter)×20 mm (length). Syringes were transferred to a water bath with temperature 37° C. for 2 hours prior to the experiment to incubate the clots. All clots were then carefully removed from syringes, weighed, and transferred to a 0.9% room temperature (21° C.), air-saturated saline solution. All clots were treated within 6 hours of addition of $CaCl_2$. The resulting clots prior to treatment had a mean mass of 331+/−39.8 mg for those used in the static vessel model. Clots for the flow model were formed on a loose string by mounting the string longitudinally in the syringe. The string with the attached thrombus was removed after clotting, and the ends of the string were fixed to the tube. This technique was used to hold the clot in place under flow during the experiment.

B. In-Vitro Static Vessel Model

A stationary vessel model with no background fluid flow was employed for assessment of thrombolysis (FIG. 1). The model used a 6-mm diameter, 60-mm length low-density polyethylene (LDPE) tube with wall thickness of 500 μm to act as a vessel holding the clot. The LPDE plastic has an acoustic impedance similar to that of tissue. The tube was filled with 0.9% saline and the clot was carefully transferred to the tube. Tapered silicone rubber stoppers were used to plug the ends of the tube to contain the saline and clot debris from the treatment.

C. Ultrasound Generation and Treatment

The histotripsy treatment was performed using a piezocomposite 1-MHz focused transducer (Imasonic, S.A., Besancon, France) with a 15-cm focal length and 15-cm diameter. The focal volume is cigar-shaped, with dimensions 15 mm along the axis of propagation and 2.0 mm laterally at −3 dB peak negative pressure of 12 MPa. The therapy transducer has a 4-cm diameter hole in the middle for inserting an imaging probe. A class D amplifier used to drive the transducer. Ultrasound was pulsed using 5-cycle bursts at a pulse repetition frequency (PRF) of 1 kHz. Ultrasound was applied to clots at different peak negative pressures of 2, 4, 6, 8, 10, and 12 MPa with corresponding spatial peak pulse average intensities ($I_{SPPA}$) of 150, 600, 2000, 3600, 5900, and 7000 W/cm². Pressure values for the ultrasound were obtained from waveforms recorded using a fiber optic probe hydrophone built in house. The probe was mounted with the fiber end facing perpendicular to the ultrasound propagation to prevent cavitation from corrupting measurements or damaging the tip. The signal was averaged over 200 pulses to reduce noise. Recorded signals are shown in FIG. 2. No deconvolution was applied to the recorded waveforms.

All treatments were performed at room temperature (21° C.), in a degassed water tank with dimensions 100 cm×75 cm×67.5 cm. The transducer was mounted to a 3-axis motorized positioning system (Velmex, Inc., Bloomfield, N.Y.) controlled by a personal computer. The positioning system was used to position the clot in the transducer focus. Ultrasound was applied until the entire clot was dissolved or 300 seconds of treatment had occurred. The transducer focus was fixed throughout the treatment and the clot naturally moved into the focus until it was completely dissolved. The thrombolysis rate was calculated as the difference in initial mass and final mass of the clot divided by the amount of time ultrasound was applied (total treatment time).

D. Cavitation Monitoring Using Acoustic Backscatter

Acoustic backscatter from the cavitating bubble cloud was passively received using a 2.5-cm aperture 5-MHz focused single-element transducer with focal length of 10 cm (Valpey Fisher Corp., Hopkinton, Mass.). It was connected directly to an oscilloscope (Lecroy, Chestnut Ridge, N.Y.) for data collection. The backscatter signal was recorded by the oscilloscope every 300 ms in a 20 µs window timed to capture the scattered therapy pulse. Tissue fractionation only occurs when initiation of a temporally changing acoustic backscatter is detected corresponding to formation of a cavitating bubble cloud. Here the initiation of the temporally changing scattered wave was detected. The backscatter receiver was positioned facing 90° from the therapy transducer instead of through the central hole of the therapy transducer, since the hole was occupied by an imaging probe. This technique measures the continuous dynamic change in scattering energy due to pulse-to-pulse changes in the bubble cloud. Briefly, the normalized energy for each backscatter waveform is calculated. A moving standard deviation over time of the normalized energy is then calculated. When this standard deviation (pulse-to-pulse variation in backscatter) is above a set threshold for 3 or more consecutive points, initiation of a bubble cloud occurs. It should be understood that other predetermined thresholds can be established to quantify the initiation of the bubble cloud. From this, the total amount of time a bubble cloud was present during treatment for each trial could be calculated. The initiation threshold for each pressure level was determined by linear extrapolation from measurements at the lowest pressure levels, where no initiation was observed.

E. Ultrasound Imaging Feedback

A 5-MHz ultrasound imager (System FiVe, General Electric, U.S.A) was used for targeting the clot and monitoring treatment progress. The imager was positioned through the central hole in the therapy transducer such that it always imaged the therapy plane. For targeting prior to treatment, a bubble cloud was generated at the focus of the transducer in the empty water bath and appeared as a hyperechoic zone, which refers to a region with increased amplitude on an ultrasound image. The position of the hyperechoic zone was marked on the image as the focus. Once the tube containing the clot was added to the water bath, the therapy transducer was positioned so that the focus marker was aligned at one end of the clot. Once the targeting is achieved, histotripsy treatment was applied to the clot. The treatment progress and completion was monitored through reduced echogenicity on the B-Mode image resulting from breakup of the clot.

F. Measurement of Histotripsy Clot Debris

There is a concern that the clot fragments or debris generated by histotripsy may form emboli and occlude downstream vessels. To address this issue, the suspended clot debris was serially filtered through 1 mm, 100 µm, 20 µm, and 5 µm filters after treatment to measure the total weight of particles in each size category. The dry weight of each filter was measured prior to treatment. After filtering, the samples were dried over 12 hours, and each filter was reweighed.

To obtain a more sensitive measurement of particle distribution, the suspended clot debris from the stationary vessel model was also measured using a particle sizing system, a Coulter Counter (Multisizer 3, Beckman Coulter, Fullerton, Calif.). After treatment, the clot debris saline suspension was collected from each of the treated clots and the debris size distribution was measured using the Coulter Counter. This device measures the impedance change due to the displacement by the particle volume of a conducting liquid in which the particles are suspended. The impedance change is proportional to the particle volume. Volume of debris particle is calculated and diameter is estimated assuming a spherical shape for each particle. The measurement size range is 2-60% of the size of aperture tube which is part of the Coulter Counter. A 100-µm diameter aperture tube was used to achieve a dynamic range of 2-60 µm in diameter. Debris larger than 60 µm which blocked the aperture tube caused interruption of the measurement, and was noted. The sizing resolution is approximately 1% of the particle diameter. Two measurements were taken for each sample.

G. Thrombolysis in a Pulsatile Flow Model

To test the effect of high flow rates on histotripsy thrombolysis, clots were treated in a circulatory model with filtered water (FIG. 1). The flow model used a pulsatile flow pump (Harvard Apparatus Pulsatile Blood Pump, Holliston, Mass.) with settings to control the pulses per minute and stroke volume. The pump was attached with vinyl tubing to one end of the vessel-mimicking LPDE tube in a water bath to allow flow into the tube. 1-mm and 100-µm rated filter paper was placed downstream from the tube to capture large clot debris and fragments. The pulsatile pump was set to operate at 70 beats per minute (bpm) with a stroke volume of 15 mL and a systolic to diastolic ratio of 35:65. These values were chosen to produce a mean flow velocity of 50 cm/sec in the 6 mm diameter LPDE tube, which is an upper limit for mean blood flow velocities typically found in major vessels.

Clots were formed on a string, as previously described. Both ends of the string were secured to hold the clot in position under flow. The transducer focus was scanned along the clot in the direction opposite of flow at a rate of 0.1 mm/s. After treatment, any remaining clot was removed from the tube and weighed to calculate the thrombolysis rate.

Results

A total of 56 clots were treated in the stationary model. At peak negative pressures (p−) of 2 and 4 MPa, no visible clot disruption was observed. At p− of 6 and 8 MPa, the clot was partially fractionated into tiny debris after 300 seconds of histotripsy treatment. At p− of 10 and 12 MPa, the entire clot was always completely fractionated within 300 seconds of treatment. Clot disruption was only observed visually when a bubble cloud was initiated at the focus of the transducer. If the bubble cloud was generated adjacent to the clot (within 10 mm), the clot would naturally move towards the bubble cloud until the center of the clot was aligned with the bubble cloud. During thrombolysis, the color of the clot changed from red to white at the surface where it was eroded, and then further dissolved until no visible fragments remained. This suggests red blood cells were destroyed prior to breakdown of the extracellular clot matrix. The progression of a treatment is shown in FIG. 3.

Section A reports the change in thrombolysis rate with acoustic pressure. Thrombolysis rate is also correlated with acoustic backscatter in section B, which reports the initiation detection of a cavitating bubble cloud at different pressures. Further, Section C describes how treatment was monitored using imaging feedback. Section D reports the size distribution of debris generated during thrombolysis. Section E shows results from performing histotripsy thrombolysis under fast circulatory flow. Finally, Section F demonstrates the ability of histotripsy to effectively trap free clot particles and further fragment them.

A. Thrombolysis Rates Versus Pressure

The thrombolysis rate was plotted as a function of peak negative pressure (p−=0 to 12 MPa) in FIG. 4A (mean and standard deviation, n=8). The corresponding peak positive pressure and $I_{SPPA}$ are listed in Table 1.

TABLE 1

Number of trials with bubble cloud initiation and significant thrombolysis at each pressure level. (n = 8 at each pressure)

| P− (Mpa) | P+ (Mpa) | Isppa (W/cm$^2$) | Istpa (W/cm$^2$) | Clot Weight (Pre) (mg) | Clot Weight (Post) (mg) | # Trials with Thrombolysis* | # Trials with Initiation |
|---|---|---|---|---|---|---|---|
| 0  | 0  | 0    | 0    | 340 ± 38 | 300 ± 40  | 0 | 0 |
| 2  | 3  | 150  | 1    | 320 ± 54 | 285 ± 54  | 0 | 0 |
| 4  | 8  | 600  | 4    | 342 ± 34 | 296 ± 27  | 0 | 0 |
| 6  | 20 | 2000 | 14   | 316 ± 39 | 251 ± 73  | 4 | 7 |
| 8  | 32 | 3600 | 25.2 | 354 ± 25 | 64 ± 52   | 8 | 8 |
| 10 | 39 | 5900 | 41   | 310 ± 41 | 1.2 ± 3.5 | 8 | 8 |
| 12 | 43 | 7000 | 49   | 332 ± 32 | 1.2 ± 3.5 | 8 | 8 |

In the control group (p−=0 MPa), clots were placed in saline for 5 minutes without ultrasound exposure, and visible clot disruption was never observed. Similarly, at p− of 2 and 4 MPa, no visible changes were observed during treatment and the thrombolysis rate was not statistically different from that of the control group. The thrombolysis rate was 0.13+/−0.038 mg/sec for the control group and 0.12+/−0.047 mg/sec at pressure of 4 MPa (t-test, P=0.22). It is possible that most of the weight reduction for each of these three groups was due to handling of the clot to transfer it into and out of the tube or dissolution of clot serum into the saline.

At p−=6 MPa, 4 of 8 clots treated had rates similar to the control group (0.066+/−0.047 mg/sec). The other 4 clots had significantly higher thrombolysis rates (0.366+/−0.087 mg/sec) than control. At p−>8 MPa, a significant increase in thrombolysis rate was observed for all clots in comparison to the control group (paired t-test, P<0.0001). At the highest pressures (p− of 10 and 12 MPa), all clots were completely fractionated in times between 80-260 seconds. There was an increase in thrombolysis rate with peak negative pressure between 6-12 MPa (t-test, P<0.05). The mean rate was 0.21+/−0.17 mg/sec at p− of 6 MPa and 2.20+/−0.85 mg/sec at p− of 12 MPa.

B. Cavitation Monitoring Using Acoustic Backscatter

Detection of temporally changing acoustic backscatter was used to monitor a cavitating bubble cloud. Without the initiation and maintenance of this temporally changing backscatter, no tissue fractionation was generated by histotripsy. It was determined that without initiation, no thrombolysis was observed, i.e., the thrombolysis rate was similar to the control rate. In 28 of 31 treatments (90%) where initiation was detected, the thrombolysis rate was significantly higher than the control. Table 1 shows the number of events for each pressure where thrombolysis occurred, as well as the number of events where initiation occurred. For purposes of discussion, thrombolysis was considered to have occurred when the thrombolysis rate was greater than twice the control rate.

The percentage of time a bubble cloud was initiated throughout treatment was calculated. The percentage of initiated time is the amount of time that temporally changing acoustic backscatter is detected divided by the total treatment time. The percentage of initiated time was plotted as a function of peak negative pressure (FIG. 4B). P− of 2-4 MPa had very low mean values for percentage of initiated time (<0.5%) and thrombolysis was never observed at these pressure levels. P− of 6 MPa had an intermediate percentage of initiated time of 56%. At this value, 4 clots where thrombolysis occurred also had a high percentage of initiated time (mean 87%) versus 4 with low thrombolysis rates (mean 25%). For 8-12 MPa, the mean percentage of initiated time was >99.6% and thrombolysis always occurred. This supports the claim that the cavitation cloud is necessary for histotripsy thrombolysis.

The thrombolysis rate at P−=6 MPa was previously defined as the mass loss divided by the total treatment time. However, it was shown that during only 56% of the treatment time was a bubble cloud present. To obtain an estimate of the thrombolysis rate only when a cloud is initiated, the total initiated time can be used to calculate rate instead of total treatment time. This calculation gives a thrombolysis rate of 0.58+/−0.17 mg/sec, which is significantly higher than the thrombolysis rate calculated using the treatment time. Since thrombolysis appears to only occur when the bubble cloud is initiated, this rate provides a better measure for the efficiency of the bubble cloud.

C. Ultrasound Imaging

The histotripsy thrombolysis treatment was monitored with B-mode ultrasound imaging in real-time. Prior to application of ultrasound, the clot appeared as a hyperechoic zone inside the tube walls on the B-mode ultrasound image (FIG. 5A). During the treatment, a bubble cloud was generated in the tube adjacent to the clot, which appeared as a temporally changing hyperechoic zone at the therapy transducer focus (FIG. 5B). Interference of the therapy acoustic pulses with the imager caused only minimal corruption of the image due to the low duty cycle used for treatment (0.5%). As the treatment progressed, the clot's hyperechoic zone reduced in size and echogenicity. The bubble cloud remained on the clot surface throughout the treatment. Once the clot was entirely fractionated, its hyperechoic zone on the image disappeared and the inside of the tube became hypoechoic (FIG. 5C).

D. Measurement of Histotripsy Clot Debris

To obtain the size distribution of clot debris generated by histotripsy, samples were measured using filter papers rated to 5 μm, 20 μm, 100 μm and 1 mm. The wet and dry weights of several whole clots were recorded. Whole clots with a wet weight of 350 mg were reduced to 100 mg weight once dried. The change in dry weight of the filter was measured to estimate the debris size distribution. All four filters' dry weights changed by <1 mg. No significant difference was found between control and any of the treated samples. These results suggest that at least 96% (96 mg of 100 mg) of the clot was broken down to particles smaller than 5 µm.

Additionally, saline samples containing suspended clot debris were removed from the tube after each treatment and measured by the Coulter Counter. The mean debris distributions between 2-60 µm particle diameter are shown in FIG. 6. For control clots, a mean of 95%+/−4% of the debris volume was between 2-10 µm, 3% between 10-30 µm, and 2% between 30-60 µm. In treatment samples where thrombolysis was detected, 72-94% of the debris was 2-10 µm, and 3-12% was between 30-60 µm. The mean number of particles counted in the treatment samples was similar to the controls. Samples treated at the highest pressures (10 and 12 MPa) had a higher percentage of larger particles (30-60 µm) than lower pressures. Debris distributions also showed a large increase in particles smaller than 6 µm for those treated at high pressures, suggesting the disruption of individual cells.

In 2 of 56 measurements (two measurements per treatment) where thrombolysis was not detected, the 100 µm tube was blocked. In 9 of 56 measurements where thrombolysis was detected, the 100 µm tube was blocked. The blockage of the tube suggested the presence of one or more particles larger than 60 µm. These results suggest that particles larger than 60 µm are generated during the treatment, although some of them may result from process other than histotripsy thrombolysis.

E. Thrombolysis Under Flow

Since cavitation may be influenced by the presence of flow, e.g., cavitation nuclei may be swept away, the feasibility of histotripsy thrombolysis was also tested in a fast flow environment. Clots were treated under a mean flow velocity of 50 cm/s. This value is the upper limit of mean flow velocities in major vessels. Clots formed for this experiment were smaller (150+/−26 mg) than those used in the stationary clot model due to difficulty forming large clots on the string. Eight clots were treated at p−=12 MPa, and clot weight was reduced by 72%+/−21% (mean and standard deviation) in the fast flow in 100 seconds. During this time, the therapy focus was scanned to cover the entire clot at a scanning rate of 0.1 mm/sec. The thrombolysis rate was 1.07.+/−0.34 mg/s, which is significantly higher than the control rate of 0.27+/−0.12 (t-test, P<0.0002). However, the rate at p−=12 MPa here was lower than those in static saline at the same pressure level.

Serial filters of 1 mm and 100 µm were used to capture any large clot debris or fragments generated by histotripsy treatment. No measurable debris was captured by the 1 mm filter. In two of the eight treated clots, 5% and 12% of the initial clot weight was captured by the 100 µm filter paper. In one of eight control clots, 17% of the clot weight was captured by the 100 µm filter. All other filters showed less than 3% variance in weight before and after the experiment.

F. Acoustic Manipulations

The acoustic manipulations have been demonstrated the in vitro experiments. For example, preliminary results show that when a clot fragment flows into the cavitating bubble cloud generated by histotripsy in a vessel tube, it can be stopped (and trapped) near the cloud and further fractionated into small debris. Clot fragments of diameter 3 mm were cut from formed clots, and injected into the circulatory model with a background flow of ~5 cm/s and upstream from the transducer focus. In the example shown in FIG. 7, a bubble cloud was generated in the tube center using p− of 12 MPa. The bubble cloud occupied approximately ⅓ of the vessel tube diameter. The 3 mm clot fragment drifted into the bubble cloud and became trapped near the transducer focus. While trapped in the cloud, the clot was further fractionated. Within one minute from when the clot fragment entered the bubble cloud, it was completely broken down with no visible fragments remaining.

This experiment was repeated 13 times to test the ability of histotripsy to capture clot fragments that would potentially be hazardous emboli. Of the 13 trials, all clots were stopped as they drifted into the bubble cloud. The clot fragments were further fractionated to smaller particles which were then ejected from the cloud. The largest particles ejected from the cloud were sub-millimeter. When the clot fragments were captured, 7 of the 13 clots were completely fractionated in a time of 142+/−99 seconds. 5 of 13 clots were partially fractionated before being swept out of the tube. They were held near the bubble cloud for a mean time of 132+/−66 seconds. 1 of 13 clots was held near the bubble cloud for 5 seconds, but was then swept downstream by background flow and remained unfragmented.

Discussion

Current clinical thrombolysis methods, including catheter-based procedures and thrombolytic drugs, have major drawbacks. Both these methods can cause severe bleeding and catheters are invasive and can cause infection. Ultrasound-enhanced thrombolysis may increase the reperfusion rate, but can also cause bleeding, as it involves the use of thrombolytic drugs. Histotripsy does not require drugs and is non-invasive, and thus has the potential to overcome these limitations. In addition, results show that histotripsy can dissolve 300 mg clots in 1.5-5 minutes. The thrombolysis rates demonstrated from in-vitro experiments are order of magnitude faster than those for drugs. Since histotripsy is non-invasive and does not involve a complex procedure to insert catheter into the treatment region, it would also require less time and lower cost than a surgical catheter.

In connection with the present disclosure, ultrasound by itself was applied to cause thrombolysis. Previous researchers explored the use of high-intensity focused ultrasound alone to break down blood clots. Rosenschein suggested that cavitation collapses were the underlying cause of damage. Cavitation has been and is still generally regarded as uncontrollable and unpredictable. The mechanism of cavitation has been studied and found that it can be well controlled using specific ultrasound pulse sequences to produce targeted fractionation of soft tissue including blood clots. A histotripsy pulse sequence includes very short pulses (<50 µs) at very high pressures (>6 MPa) and low duty cycles (0.1-5%). Our hypothesis regarding the mechanism of histotripsy is that each ultrasound pulse creates a cluster of microbubbles localized at the transducer focus. The microbubbles within the cluster collapse causing local stresses which remove a portion of the targeted tissue. These individual microbubbles also act as nuclei which can be excited by subsequent pulses, predisposing tissue in the focal region to further damage. It has been found that tissue fractionation only occurs with the initiation and maintenance of a cavitating bubble cloud, which can be achieved using appropriate ultrasound pulse sequences (i.e., histotripsy pulses). Bubble cloud initiation and maintenance can be detected by cavitation feedback monitoring. Cavitation feedback includes ultrasound imaging and acoustic backscatter signals with specific traits, such as high temporally-changing backscatter amplitudes and increased broadband noise levels.

Accordingly, our understanding of histotripsy is consistent with the results from the present disclosure. It has thus been found that thrombolysis only occurs when the cavitating bubble cloud is detected by acoustic backscatter. The acoustic parameters effective for thrombolysis are also consistent with the parameters found effective for other soft tissue fractionation, using short pulses, a low duty cycle, and a peak negative pressure >=6 MPa. While a correlation between the cavitating bubble cloud and the fractionation of tissue has been demonstrated, how individual bubbles interact with the targeted tissue to cause fractionation is not sufficiently understood. A variety of damage mechanisms have been proposed, including collapse of individual microbubbles, bubble cloud collapse, microstreaming-induced shear forces and acoustic streaming, or combinations of these effects.

One major advantage of histotripsy is that it can be easily guided by real-time ultrasound imaging for targeting and treatment monitoring. The results suggest that histotripsy thrombolysis can be also guided using real-time ultrasound imaging. The bubble cloud is highly echogenic and dynamic on a B-mode image, and blood clots can be readily identified and aligned to the therapy focus. The progression of thrombolysis can also be monitored by observing clot echogenecity and Doppler color flow mapping of the occluded vessel. Using these techniques, histotripsy thrombolysis can be visualized and guided by real-time ultrasound imaging feedback, which is a primary challenge for any non-invasive technique and essential to ensure the treatment accuracy and efficiency.

As bubble dynamics are highly dependent on their environment, there is a possibility that the effects of histotripsy may be hindered by high blood flow velocities. The maintenance of a bubble cloud likely depends on previously initiated nuclei, and those nuclei may be swept out of the focus by background flow. The feasibility of histotripsy thrombolysis at the highest natural flow velocity in-vivo (50 cm/sec) was studied. When clots were subjected to a high-velocity pulsatile flow, histotripsy was still capable of fractionating the clot. This result shows that a cavitation cloud can be initiated and maintained in the fast flow. In this situation, the thrombolysis rate was lower than those treated without flow. This could be because the clot is held in a fixed position in the flow model, and the transducer focus must scan along the clot to completely fractionate it. Since the scanning velocity may not have been optimized, some of the clot remained intact after treatment in several cases.

Since histotripsy causes damage by microbubbles that are very small (particularly when they collapse), histotripsy can fractionate tissue to tiny debris. When histotripsy is used to treat soft tissues (e.g., kidney, myocardium, and prostate), it fractionates tissue to a sub-cellular level with debris of a few microns or smaller. Similarly, histotripsy can fractionate a blood clot into small debris. The filter measurements suggest >96% of the debris weight was smaller than 5 µm. The Coulter Counter method also showed that small particles (2-10 µm) were a majority (74-94%) of debris in the range of 2-60 µm. The fact that the number of particles counted in both control and treated samples was similar suggests that a majority of debris generated by histotripsy is outside of the Coulter Counter range (i.e., likely smaller than 2 µm). Both the filter and Coulter Counter measurements indicated that histotripsy breaks down the clot below the size of individual red blood cells (6-8 µm). 100 µm mechanical filters have been used to successfully prevent embolism, and only particles larger than this may be considered potentially unsafe emboli. The Coulter Counter measurement suggests that there are occasionally debris particles larger than 100 µm. Debris generated at lower pressures (6 and 8 MPa) also contained fewer large fragments than higher pressures. It is possible that the acoustic parameters could be adjusted to minimize the number of large particles. However, it is not clear that whether particles >100 µm can be avoided completely during treatment.

A method to reduce the risk of embolism was tested, using a bubble cloud to capture and fractionate the emboli. In the preliminary test, the bubble cloud could be used to trap a large clot particle near the focus and further fragment it. This acoustic trapping ability is likely due to cavitation-induced fluid flow. Microstreaming can generate a flow pattern pulling particles towards a single bubble even in the presence of an overall directional flow. This phenomenon is also applicable (and may be magnified) when bubbles act collectively as a cloud. Using the acoustic trapping property of histotripsy, development of a Non-invasive Embolus Trap (NET) is anticipated, which is a secondary cavitating bubble cloud set downstream of the primary treatment cloud to capture and further fractionate any escaping clot fragments. The NET could be created by a separate transducer and effectively act as a filter for large emboli. Preliminary tests indicated that clot fragments can be trapped and further broken down into smaller fragments. In some embodiments, the observed bubble cloud was only ⅓ of the tube diameter and did not occupy the whole tube. Its small size is possibly why some fragments escaped from the cloud before complete fractionation and a significant amount of debris larger than 100 um were measured. By applying appropriate acoustic parameters, the bubble cloud size can be changed to occupy a larger portion of the tube and maintain greater control over particles. It is possible that different sets of parameters will be optimal for the NET than for the thrombolysis treatment. The NET would add an additionally degree of safety to the treatment, and may be an effective means to prevent embolism in other procedures that may be associated with the risk of embolization.

Aside from embolism, there are other concerns that must be addressed regarding the safety of histotripsy thrombolysis. As histotripsy mechanically fractionates a clot, there is a possibility that the process might also damage the surrounding blood vessel. As part of the present disclosure, clots were treated in a canine aorta segment and vena cava segment using the same acoustic parameters as discussed herein at a pressure level of p−=12 MPa. FIG. 8 shows the histology of control and treated segments after 300 seconds of exposure. Histotripsy-treated aorta and vena cava walls remained intact in initial histological studies. The vessel's higher resistance to histotripsy-induced damage is likely due to its mechanical ductility being higher than that of soft tissues. In addition to mechanical damage, the vessel may also be damaged by ultrasound-induced heating. However, histotripsy uses a very low duty cycle and the time-averaged intensity at the focus is lower than that required to cause thermal necrosis.

Hemolysis may also be an adverse effect of histotripsy thrombolysis. Red blood cells are easily damaged by shear forces, and have been previously shown to be susceptible to cavitation. The debris measurements suggest that histotripsy breaks down red blood cells within the clot to subcellular fragments. Therefore, it is also likely that free erythrocytes in blood will also be lysed. When hemolysis occurs in a significant volume of blood, it can cause hemolytic anemia and hyperkalemia. As the treatment is only localized to the small focal volume and the flow rates in occluded vessels are generally low, it is unlikely that large volumes of blood will be lysed during the treatment. Ultrasound (and cavitation in particular) has also been observed to cause platelet aggregation and activation, which facilitates clotting. There is a possibility that histotripsy may cause clot reformation by activating platelets.

CONCLUSION

The results show that histotripsy mechanically fractionates blood clots into small particles. Histotripsy can completely remove large clots in both a controlled static saline environment and a fast flow model simulating in vivo blood flow. In both cases, the treatment time lasted less than five minutes for large clot (140-300 mg). Thrombolysis only occurred when the presence of a dense cavitation cloud was detected. Debris particles generated by histotripsy thrombolysis was measured and revealed >96% particle weight smaller than 5 µm, although some particles >100 µm were generated. To address this issue, the ability of histotripsy to trap and further fractionate large clot fragments was tested. It was found that the cavitating bubble cloud can capture and simultaneously fractionate a clot fragment flowing through the cloud. This ability may provide a novel tool to capture and eliminate hazardous emboli by setting a secondary bubble cloud downstream of the treatment cloud. These findings suggest that histotripsy is a viable new thrombolysis strategy.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A method for controlled mechanical fractionation of a thrombus, said method comprising:

outputting an initiation ultrasound pulse sequence with a therapy transducer to form an initial bubble cloud positioned away from the thrombus;

detecting a location of the initial bubble cloud under real-time imaging to determine a therapy focus of the therapy transducer;

moving the therapy transducer to align the therapy focus with the thrombus;

after the moving step, outputting the initiation ultrasound pulse sequence from the therapy transducer to form a therapy bubble cloud within the therapy focus;

detecting the therapy bubble cloud under real-time imaging as the therapy bubble cloud is generally aligned with at least a portion of the thrombus;

outputting a bubble cloud sustaining ultrasound pulse sequence from the therapy transducer to maintain the therapy bubble cloud and produce at least partial fractionation of the thrombus; and imaging thrombus treatment progression and completion under real-time imaging.

2. The method of claim 1, wherein the real-time imaging comprises B-mode ultrasound imaging.

3. The method of claim 1, wherein said imaging thrombus treatment progression further comprises detecting fractionation of the thrombus.

4. The method of claim 3, wherein said detecting fractionation of the thrombus comprises detecting reduced echogenicity on a B-Mode ultrasound image.

5. The method of claim 4, wherein said detecting fractionation of the thrombus comprises detecting changes in ultrasound Doppler color flow downstream of a treatment region on an ultrasound image.

6. The method of claim 1, wherein the initiation ultrasound pulse sequence comprises a peak negative pressure of >=6 MPa, a peak positive pressure of >=8 MPa, a pulse length shorter than 50 cycles, and a duty cycle between approximately 0.1% and 5%.

* * * * *